US006465714B2

(12) United States Patent
Luthman et al.

(10) Patent No.: US 6,465,714 B2
(45) Date of Patent: *Oct. 15, 2002

(54) CONGENIC ANIMAL MODELS OF NON-INSULIN DEPENDENT DIABETES MELLITUS

(75) Inventors: L. Holger Luthman, Bromma; L. G. Joakim Galli, Taby, both of (SE)

(73) Assignee: Arexis AB (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/434,066

(22) Filed: Nov. 5, 1999

(65) Prior Publication Data

US 2002/0035733 A1 Mar. 21, 2002

(51) Int. Cl.[7] .................. A01K 67/00; A01K 67/033; A01K 67/027; G01N 33/00; C12N 15/00
(52) U.S. Cl. ................... 800/9; 800/3; 800/14; 800/22; 435/325
(58) Field of Search .................. 800/3, 9, 14; 435/325, 435/22; 536/23.1

(56) References Cited

U.S. PATENT DOCUMENTS

| 5,614,396 A | 3/1997 | Bradley et al. .......... 435/172.3 |
| 5,795,726 A | 8/1998 | Glucksmann .............. 435/7.21 |

FOREIGN PATENT DOCUMENTS

| WO | WO 91/19796 | 12/1991 |
| WO | WO 98/23145 | 6/1998 |
| WO | WO 99/35169 | 7/1999 |

OTHER PUBLICATIONS

Ebert el al, 1988, Mol. Endocrinol., 2: 277–283.*
Hammer et al, 1986, J. Anim. Sci., 269–278.*
Houdebine et al, 1994, J. Biotechnol., 34: 269–287.*
Kappel et al, 1992, Cur. Opin. Biotech., 3: 548–553.*
Mullins et al, 1996, J. Clin. Invest., 98: S37–40.*
Strojek et al, 1988, Genetic Engineering: Principles and methods, Plenum Press, 10: 221–246.*
Wall et al, 1996, Theriogenology, 45: 57–68.*
Grisanti et al, 1997, Invest. Ophthalm. Vis. Sci., 38(8): 1619–1626.*
Affholter et al., "Human Insulin–Degrading Enzyme Shares Structural and Functional Homologies with *E. coli* Protease III," *Science*, 1988, 242:1415–1418.
Becker and Roth, "An unusual active site identified in a family of zinc metalloendopeptidases," *Proc. Natl. Acad. Sci. USA*, 1992, 89:3835–3839.
Joshi et al., "Genetically engineered mice as animal models for NIDDM," *FEBS Letters*, 1997, 401:99–103.
Kuo et al., "Insulin–Degrading Enzyme is Differentially Expressed and Developmentally Regulated in Various Rat Tissues," *Endocrinology*, 1993, 132(2):604–611.
Fakhrai–Rad et al., *Human Mol. Genetics*, 2000, 9(14):2149–2158.
Galli et al., *Diabetes*, 1999,48(12):2463–2470.
Abdel–Halim et al., *Diabetes*, 1994, 43:281–288.
Authier et al., *Clin. Invest. Med.*, 1996, 19(3):149–160.
Baumeister et al., *FEBS Letters*, 1993, 317(3):250–254.
Bisbis et al., *Am. J. Physiol.*, 1993, 265(5):E807–E813.
Darvasi et al., *Genetics*, 1995, 141(3):1199–1207.
Darvasi, *Mamm. Genome*, 1997, 8(3):163–167.
Darvasi, *Nat. Genet.*, 1998, 18(1):19–24.
Galli et al., *Nat. Genet.*, 1996, 12(1):31–37.
Gauguier et al., *Nat. Genet.*, 1996, 12(1):38–43.
Goto et al., *Proc. Japan Acad.*, 1975, 51:80–85.
Hughes et al., *Diabetologia*, 1994, 37(9):863–870.
Jacob et al., *Cell*, 1991, 67(1):213–224.
Kamel et al., *Pediatr. Res.*, 1997, 41(4):563–567.
Kanemoto et al., *Mamm. Genome*, 1998, 9(6):419–425.
Kim et al., *Physiol. Pharmacol.*, 1998, 9(2–4):325–345.
Moody et al., *Horm. Metab. Res.*, 1974, 6:12–16.
Östenson et al., *Diabetologia*, 1993, 36(1):3–8.
Portha et al., *Diabetes*, 1991, 40(4):486–491.
Suzuki et al., *Lessons from Animal Diabetes*, 1993, 107–116.
Whittaker et al., *Genet. Res.*, 1995, 66(3):255–265.
Withers et al., *Nature*, 1998, 391:900–904.

* cited by examiner

*Primary Examiner*—Deborah J. Reynolds
*Assistant Examiner*—Peter Paras, Jr.
(74) *Attorney, Agent, or Firm*—Fish & Richardson, P.C., P.A.

(57) ABSTRACT

Congenic animals and animal populations having type II diabetes-associated phenotypes are described. Insulin degradation polypeptides having amino acid substitutions linked to a type II diabetes-associated phenotypes also are described.

30 Claims, 10 Drawing Sheets

SEQUENCE LISTING

```
<160> NUMBER OF SEQ ID NOS: 23

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
tttattcatt gcagagggt                                                  20

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
gtgaccagct acaatcatag                                                 20

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
gtgccaaggt ctgaagatcc                                                 20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
gtgaccagct acagtcggaa                                                 20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
gtgccaaggt ctgaaggtca                                                 20

<210> SEQ ID NO 6
<211> LENGTH: 19
<212> TYPE: DNA
<213> ORGANISM: Artificial Sequence
<220> FEATURE:
<223> OTHER INFORMATION: primer
```

-continued

```
<400> SEQUENCE: 6
aagggcccgt ggacacgag                                          19

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
gaagagcaaa agcccacctg                                         20

<210> SEQ ID NO 8
<211> LENGTH: 22
<212> TYPE: DNA
<213> ORGANISM: Artificial Sequence
<220> FEATURE:
<223> OTHER INFORMATION: primer

<400> SEQUENCE: 8
actacagaag ttgaacactc tg                                      22

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
cgatgcccag tttgtggatg                                         20

<210> SEQ ID NO 10
<211> LENGTH: 22
<212> TYPE: DNA
<213> ORGANISM: Artificial Sequence
<220> FEATURE:
<223> OTHER INFORMATION: primer

<400> SEQUENCE: 10
actacagaag ttgaacactc tg                                      22

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
acttaggatt tggaatgagc                                         20

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
ttgggtagag ttgggttgat                                         20

<210> SEQ ID NO 13
<211> LENGTH: 21
```

```
<212> TYPE: DNA
<213> ORGANISM: Artificial Sequence
<220> FEATURE:
<223> OTHER INFORMATION: primer

<400> SEQUENCE: 13
cgaaatcatt ggctgagact g                                      21

<210> SEQ ID NO 14
<211> LENGTH: 21
<212> TYPE: DNA
<213> ORGANISM: Artificial Sequence
<220> FEATURE:
<223> OTHER INFORMATION: primer

<400> SEQUENCE: 14
gggtactctt ctgaactgtg g                                      21

<210> SEQ ID NO 15
<211> LENGTH: 21
<212> TYPE: DNA
<213> ORGANISM: Artificial Sequence
<220> FEATURE:
<223> OTHER INFORMATION: primer

<400> SEQUENCE: 15
tggcttctgt cttcttcttg g                                      21

<210> SEQ ID NO 16
<211> LENGTH: 21
<212> TYPE: DNA
<213> ORGANISM: Artificial Sequence
<220> FEATURE:
<223> OTHER INFORMATION: primer

<400> SEQUENCE: 16
ctgcttcctt acctgtcctt a                                      21

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
agctggtgga caaacaggag                                        20

<210> SEQ ID NO 18
<211> LENGTH: 22
<212> TYPE: DNA
<213> ORGANISM: Artificial Sequence
<220> FEATURE:
<223> OTHER INFORMATION: primer

<400> SEQUENCE: 18
gtgaacctgc tgattaacta ag                                     22

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
```

```
ctgtttgtct ctctaattgc                                                      20

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
atgcggaacg ggctcgtgtg                                                      20

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
agccagaaac tactcaaagc                                                      20

<210> SEQ ID NO 22
<211> LENGTH: 4276
<212> TYPE: DNA
<213> ORGANISM: Rattus norvegicus
<220> FEATURE:
<221> NAME/KEY: CDS
<222> LOCATION: (16)...(3075)

<400> SEQUENCE: 22
gcggctgcgc ggggt atg cgg aac ggg ctc gtg tgg ctg ctg cac ccc gcg         51
               Met Arg Asn Gly Leu Val Trp Leu Leu His Pro Ala
                 1               5                  10 ctg ccc agc acc ttg cac tcc atc ctc ggc gct cgc ccg cct ccc gtg          99
Leu Pro Ser Thr Leu His Ser Ile Leu Gly Ala Arg Pro Pro Pro Val
         15                  20                  25 aag cga ctg tgt gga ttc cca aaa caa att tac agc aca atg aat aat         147
Lys Arg Leu Cys Gly Phe Pro Lys Gln Ile Tyr Ser Thr Met Asn Asn
 30                  35                  40 ccg gcc atc cag aga ata gaa gac cat att gtc aag tct cct gaa gac         195
Pro Ala Ile Gln Arg Ile Glu Asp His Ile Val Lys Ser Pro Glu Asp
 45                  50                  55                  60 aaa cgg gaa tat cgt gga cta gaa ctg gcc aat ggt atc aaa gtg ctt         243
Lys Arg Glu Tyr Arg Gly Leu Glu Leu Ala Asn Gly Ile Lys Val Leu
                 65                  70                  75 ctc atc agt gat ccc acc acg gac aag tca tca gca gca ctc gac gtg         291
Leu Ile Ser Asp Pro Thr Thr Asp Lys Ser Ser Ala Ala Leu Asp Val
         80                  85                  90 cac ata ggg tca ctg tca gac cct cca aat att cct ggc tta agc cat         339
His Ile Gly Ser Leu Ser Asp Pro Pro Asn Ile Pro Gly Leu Ser His
         95                 100                 105 ttt tgt gag cat atg ctg ttt ttg gga aca aag aaa tat cct aag gaa         387
Phe Cys Glu His Met Leu Phe Leu Gly Thr Lys Lys Tyr Pro Lys Glu
        110                 115                 120 aat gaa tac agc cag ttt ctc agt gaa cat gct ggg agt tca aat gca         435
Asn Glu Tyr Ser Gln Phe Leu Ser Glu His Ala Gly Ser Ser Asn Ala
125                 130                 135                 140 ttt acc agc gga gaa cac acc aat tat tat ttc gat gtt tcc cat gaa         483
Phe Thr Ser Gly Glu His Thr Asn Tyr Tyr Phe Asp Val Ser His Glu
                145                 150                 155 cac ttg gaa gga gcc ctg gac agg ttt gcc cag ttt ttc ctg tgc ccc         531
His Leu Glu Gly Ala Leu Asp Arg Phe Ala Gln Phe Phe Leu Cys Pro
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 160 |     |     |     |     | 165 |     |     |     |     |     | 170 |     |     |      |
| ttg | ttt | gat | gca | agt | tgt | aag | gac | aga | gag | gtg | aac | gct | gtc | gat | tca | 579  |
| Leu | Phe | Asp | Ala | Ser | Cys | Lys | Asp | Arg | Glu | Val | Asn | Ala | Val | Asp | Ser |      |
|     |     | 175 |     |     |     |     | 180 |     |     |     |     |     | 185 |     |     |      |
| gag | cat | gaa | aag | aat | gtg | atg | aat | gat | gcc | tgg | aga | ctc | ttc | cag | ctg | 627  |
| Glu | His | Glu | Lys | Asn | Val | Met | Asn | Asp | Ala | Trp | Arg | Leu | Phe | Gln | Leu |      |
|     | 190 |     |     |     |     | 195 |     |     |     |     | 200 |     |     |     |     |      |
| gaa | aag | gct | aca | ggg | aat | ccc | aag | cac | ccc | ttc | agc | aaa | ttc | ggg | aca | 675  |
| Glu | Lys | Ala | Thr | Gly | Asn | Pro | Lys | His | Pro | Phe | Ser | Lys | Phe | Gly | Thr |      |
| 205 |     |     |     |     | 210 |     |     |     |     | 215 |     |     |     |     | 220 |      |
| gga | aac | aaa | tat | act | cta | gag | act | cga | ccc | aac | caa | gaa | ggc | atc | gat | 723  |
| Gly | Asn | Lys | Tyr | Thr | Leu | Glu | Thr | Arg | Pro | Asn | Gln | Glu | Gly | Ile | Asp |      |
|     |     |     |     | 225 |     |     |     |     | 230 |     |     |     |     | 235 |     |      |
| gta | agg | gaa | gaa | ctc | ttg | aaa | ttt | cac | tct | acg | tat | tat | tcg | tcc | aat | 771  |
| Val | Arg | Glu | Glu | Leu | Leu | Lys | Phe | His | Ser | Thr | Tyr | Tyr | Ser | Ser | Asn |      |
|     |     |     | 240 |     |     |     |     | 245 |     |     |     |     | 250 |     |     |      |
| ctg | atg | gcg | att | tgt | gtt | tta | ggt | cga | gaa | tct | tta | gat | gac | ctg | act | 819  |
| Leu | Met | Ala | Ile | Cys | Val | Leu | Gly | Arg | Glu | Ser | Leu | Asp | Asp | Leu | Thr |      |
|     |     | 255 |     |     |     |     | 260 |     |     |     |     | 265 |     |     |     |      |
| aat | ctg | gtg | gtg | aag | tta | ttt | tct | gaa | gta | gag | aat | aaa | aat | gtc | cct | 867  |
| Asn | Leu | Val | Val | Lys | Leu | Phe | Ser | Glu | Val | Glu | Asn | Lys | Asn | Val | Pro |      |
| 270 |     |     |     |     | 275 |     |     |     |     | 280 |     |     |     |     |     |      |
| ttg | cct | gaa | ttt | cct | gag | cac | cct | ttc | caa | gaa | gaa | cat | ctt | aaa | caa | 915  |
| Leu | Pro | Glu | Phe | Pro | Glu | His | Pro | Phe | Gln | Glu | Glu | His | Leu | Lys | Gln |      |
| 285 |     |     |     |     | 290 |     |     |     |     | 295 |     |     |     |     | 300 |      |
| ctt | tat | aaa | ata | gta | ccc | att | aag | gat | att | agg | aat | ctt | tat | gtg | aca | 963  |
| Leu | Tyr | Lys | Ile | Val | Pro | Ile | Lys | Asp | Ile | Arg | Asn | Leu | Tyr | Val | Thr |      |
|     |     |     |     | 305 |     |     |     |     | 310 |     |     |     |     | 315 |     |      |
| ttt | ccc | ata | cca | gac | ctt | caa | cag | tac | tac | aaa | tcc | aat | ccc | ggt | cat | 1011 |
| Phe | Pro | Ile | Pro | Asp | Leu | Gln | Gln | Tyr | Tyr | Lys | Ser | Asn | Pro | Gly | His |      |
|     |     |     | 320 |     |     |     |     | 325 |     |     |     |     | 330 |     |     |      |
| tat | ctc | ggt | cat | ctg | atc | ggg | cat | gaa | ggt | cct | gga | agc | ctg | ttg | tca | 1059 |
| Tyr | Leu | Gly | His | Leu | Ile | Gly | His | Glu | Gly | Pro | Gly | Ser | Leu | Leu | Ser |      |
|     |     | 335 |     |     |     |     | 340 |     |     |     |     | 345 |     |     |     |      |
| gag | ctc | aag | tca | aag | ggc | tgg | gta | aac | acc | ctg | gtt | ggg | gga | cag | aag | 1107 |
| Glu | Leu | Lys | Ser | Lys | Gly | Trp | Val | Asn | Thr | Leu | Val | Gly | Gly | Gln | Lys |      |
|     | 350 |     |     |     |     | 355 |     |     |     |     | 360 |     |     |     |     |      |
| gaa | gga | gcc | cga | ggt | ttt | atg | ttt | ttt | atc | att | aat | gtg | gac | tta | act | 1155 |
| Glu | Gly | Ala | Arg | Gly | Phe | Met | Phe | Phe | Ile | Ile | Asn | Val | Asp | Leu | Thr |      |
| 365 |     |     |     |     | 370 |     |     |     |     | 375 |     |     |     |     | 380 |      |
| gaa | gaa | ggg | tta | tta | cat | gtt | gaa | gat | ata | att | ttg | cac | atg | ttt | caa | 1203 |
| Glu | Glu | Gly | Leu | Leu | His | Val | Glu | Asp | Ile | Ile | Leu | His | Met | Phe | Gln |      |
|     |     |     |     | 385 |     |     |     |     | 390 |     |     |     |     | 395 |     |      |
| tac | att | cag | aag | cta | cgt | gct | gaa | gga | cct | caa | gaa | tgg | gtt | ttc | caa | 1251 |
| Tyr | Ile | Gln | Lys | Leu | Arg | Ala | Glu | Gly | Pro | Gln | Glu | Trp | Val | Phe | Gln |      |
|     |     |     | 400 |     |     |     |     | 405 |     |     |     |     | 410 |     |     |      |
| gag | tgc | aag | gac | ttg | aac | gct | gtc | gct | ttc | agg | ttt | aaa | gat | aaa | gag | 1299 |
| Glu | Cys | Lys | Asp | Leu | Asn | Ala | Val | Ala | Phe | Arg | Phe | Lys | Asp | Lys | Glu |      |
|     |     |     |     | 415 |     |     |     |     | 420 |     |     |     |     | 425 |     |      |
| agg | cca | cga | ggc | tac | aca | tct | aag | att | gca | ggg | aaa | ttg | cac | tat | tat | 1347 |
| Arg | Pro | Arg | Gly | Tyr | Thr | Ser | Lys | Ile | Ala | Gly | Lys | Leu | His | Tyr | Tyr |      |
|     |     | 430 |     |     |     |     | 435 |     |     |     |     | 440 |     |     |     |      |
| ccc | cta | aat | gga | gtg | ctc | aca | gct | gaa | tat | tta | ctg | gaa | gaa | ttt | aga | 1395 |
| Pro | Leu | Asn | Gly | Val | Leu | Thr | Ala | Glu | Tyr | Leu | Leu | Glu | Glu | Phe | Arg |      |
| 445 |     |     |     |     | 450 |     |     |     |     | 455 |     |     |     |     | 460 |      |
| ccc | gac | ttg | ata | gac | atg | gtt | ctt | gat | aaa | ctc | aga | cca | gaa | aat | gtc | 1443 |
| Pro | Asp | Leu | Ile | Asp | Met | Val | Leu | Asp | Lys | Leu | Arg | Pro | Glu | Asn | Val |      |
|     |     |     |     | 465 |     |     |     |     | 470 |     |     |     |     | 475 |     |      |
| cgg | gtg | gca | ata | gtt | tct | aaa | tca | ttt | gaa | ggg | aaa | act | gac | cgc | aca | 1491 |

```
                                                   -continued

Arg Val Ala Ile Val Ser Lys Ser Phe Glu Gly Lys Thr Asp Arg Thr
            480                 485                 490 gag cag tgg tat gga acc cag tac aag caa gaa gct atc cca gag gac      1539
Glu Gln Trp Tyr Gly Thr Gln Tyr Lys Gln Glu Ala Ile Pro Glu Asp
            495                 500                 505 gtc att cag aaa tgg caa aat gct gac ctg aat ggg aaa ttt aaa ctt      1587
Val Ile Gln Lys Trp Gln Asn Ala Asp Leu Asn Gly Lys Phe Lys Leu
    510                 515                 520 cca aca aag aat gaa ttc att cct aca aat ttt gag att ttg gca tta      1635
Pro Thr Lys Asn Glu Phe Ile Pro Thr Asn Phe Glu Ile Leu Ala Leu
525                 530                 535                 540 gaa aaa gat gca aca cca tac cct gct ctt att aag gat aca gcc atg      1683
Glu Lys Asp Ala Thr Pro Tyr Pro Ala Leu Ile Lys Asp Thr Ala Met
                545                 550                 555 agt aag ctg tgg ttc aaa caa gat gat aaa ttt ttc ttg ccg aaa gct      1731
Ser Lys Leu Trp Phe Lys Gln Asp Asp Lys Phe Phe Leu Pro Lys Ala
            560                 565                 570 tgt ctc aac ttt gaa ttt ttc agc ccg ttt gct tat gtg gac ccc ttg      1779
Cys Leu Asn Phe Glu Phe Phe Ser Pro Phe Ala Tyr Val Asp Pro Leu
            575                 580                 585 cac tgt aac atg gcc tat ttg tac ctt gaa ctc ctc aaa gac tca ctc      1827
His Cys Asn Met Ala Tyr Leu Tyr Leu Glu Leu Leu Lys Asp Ser Leu
        590                 595                 600 aac gag tat gca tat gca gca gag cta gca ggc ctg agc tat gat ctc      1875
Asn Glu Tyr Ala Tyr Ala Ala Glu Leu Ala Gly Leu Ser Tyr Asp Leu
605                 610                 615                 620 caa aac acc atc tat ggg atg tat ctc tca gtg aaa ggt tac aat gac      1923
Gln Asn Thr Ile Tyr Gly Met Tyr Leu Ser Val Lys Gly Tyr Asn Asp
                625                 630                 635 aaa cag cca att ttg cta aag aag atc acc gag aaa atg gct act ttt      1971
Lys Gln Pro Ile Leu Leu Lys Lys Ile Thr Glu Lys Met Ala Thr Phe
            640                 645                 650 gag att gat aaa aaa aga ttt gaa att atc aaa gag gcg tac atg cga      2019
Glu Ile Asp Lys Lys Arg Phe Glu Ile Ile Lys Glu Ala Tyr Met Arg
            655                 660                 665 tct ctt aat aat ttc cgg gct gag cag cct cac cag cac gcc atg tac      2067
Ser Leu Asn Asn Phe Arg Ala Glu Gln Pro His Gln His Ala Met Tyr
        670                 675                 680 tac ctc cgt ctg ctg atg act gaa gtg gcc tgg acc aaa gat gag tta      2115
Tyr Leu Arg Leu Leu Met Thr Glu Val Ala Trp Thr Lys Asp Glu Leu
685                 690                 695                 700 aaa gaa gcc ctc gat gat gtg acc ctc ccc cgt ctt aag gcc ttc ata      2163
Lys Glu Ala Leu Asp Asp Val Thr Leu Pro Arg Leu Lys Ala Phe Ile
                705                 710                 715 cct cag ctg ctg tcc cgg ctg cat att gaa gcc ctt ctc cat ggc aac      2211
Pro Gln Leu Leu Ser Arg Leu His Ile Glu Ala Leu Leu His Gly Asn
            720                 725                 730 ata aca aag cag gct gcc tta gga gtt atg cag atg gta gaa gac acc      2259
Ile Thr Lys Gln Ala Ala Leu Gly Val Met Gln Met Val Glu Asp Thr
            735                 740                 745 ctt att gag cat gct cac acc aaa cct ctc ctt cca agt cag cta gtc      2307
Leu Ile Glu His Ala His Thr Lys Pro Leu Leu Pro Ser Gln Leu Val
        750                 755                 760 cgg tac aga gaa gtt cag ctc ccc gac cga gga tgg ttt gtt tac cag      2355
Arg Tyr Arg Glu Val Gln Leu Pro Asp Arg Gly Trp Phe Val Tyr Gln
765                 770                 775                 780 cgg agg aac gaa gtc cac aat aac tgt ggc att gag att tac tac cag      2403
Arg Arg Asn Glu Val His Asn Asn Cys Gly Ile Glu Ile Tyr Tyr Gln
                785                 790                 795
```

-continued

| | | |
|---|---|---|
| aca gac atg cag agc acc tcg gag aac atg ttc ctg gag ctc ttc tgc<br>Thr Asp Met Gln Ser Thr Ser Glu Asn Met Phe Leu Glu Leu Phe Cys<br>800                            805                       810 | | 2451 |
| cag att atc tct gag cct tgc ttc aac act ctg cgt acc aag gag cag<br>Gln Ile Ile Ser Glu Pro Cys Phe Asn Thr Leu Arg Thr Lys Glu Gln<br>815                       820                   825 | | 2499 |
| ctt ggc tat att gtc ttc agt gga cct cgt cgg gcc aac ggc atc cag<br>Leu Gly Tyr Ile Val Phe Ser Gly Pro Arg Arg Ala Asn Gly Ile Gln<br>830                       835                   840 | | 2547 |
| ggc ttg cga ttc atc atc cag tca gaa aaa cca cct cac tac ctg gaa<br>Gly Leu Arg Phe Ile Ile Gln Ser Glu Lys Pro Pro His Tyr Leu Glu<br>845                   850               855               860 | | 2595 |
| agc aga gtg gaa gcc ttc ttg atc acc atg gaa aag gcc ata gag gac<br>Ser Arg Val Glu Ala Phe Leu Ile Thr Met Glu Lys Ala Ile Glu Asp<br>865                       870                   875 | | 2643 |
| atg aca gag gag gct ttc caa aaa cac att cag gcg tta gcg att cgc<br>Met Thr Glu Glu Ala Phe Gln Lys His Ile Gln Ala Leu Ala Ile Arg<br>880                       885                   890 | | 2691 |
| cga ctc gac aaa cca aag aaa ctc tct gca gag tgc gcg aag tac tgg<br>Arg Leu Asp Lys Pro Lys Lys Leu Ser Ala Glu Cys Ala Lys Tyr Trp<br>895                       900                   905 | | 2739 |
| ggg gag atc atc tcc cag cag tac aat tat gac aga gat aac ata gag<br>Gly Glu Ile Ile Ser Gln Gln Tyr Asn Tyr Asp Arg Asp Asn Ile Glu<br>910                       915                   920 | | 2787 |
| gtt gca tat tta aag aca ctc agc aag gat gat atc atc aaa ttc tac<br>Val Ala Tyr Leu Lys Thr Leu Ser Lys Asp Asp Ile Ile Lys Phe Tyr<br>925                       930                   935               940 | | 2835 |
| aag gaa atg ttg gct gtg gac gca cca agg aga cat aaa gta tcc gtc<br>Lys Glu Met Leu Ala Val Asp Ala Pro Arg Arg His Lys Val Ser Val<br>945                       950                   955 | | 2883 |
| cac gtt ctt gcc agg gaa atg gat tct tgt cct gtg gtt gga gag ttc<br>His Val Leu Ala Arg Glu Met Asp Ser Cys Pro Val Val Gly Glu Phe<br>960                       965                   970 | | 2931 |
| ccc tct cag aat gat ata aac ctt tcc gaa gcg cca ccc ttg cca caa<br>Pro Ser Gln Asn Asp Ile Asn Leu Ser Glu Ala Pro Pro Leu Pro Gln<br>975                       980                   985 | | 2979 |
| cct gag gtg att cat aac atg act gaa ttc aag cgc ggc ctg ccg ctg<br>Pro Glu Val Ile His Asn Met Thr Glu Phe Lys Arg Gly Leu Pro Leu<br>990                       995                   1000 | | 3027 |
| ttc ccc ctt gtg aag cca cac att aac ttc atg gcg gca aaa ctc tga<br>Phe Pro Leu Val Lys Pro His Ile Asn Phe Met Ala Ala Lys Leu<br>1005                     1010                   1015 | | 3075 |
| agaagcagct gcgcccctgt gccttccggg gccaggaaag cagtctcagc tttgagtagt | | 3135 |
| ttctggcttg caattagaga gacaaacaga aaagagttat caggcattat tatgtagaat | | 3195 |
| gttaaaaacc caaagtaata aaattataaa gtcttataga tgtagaatat ttttaaaatc | | 3255 |
| tcttaaatat tttaatgttt ttcttttttat tcctaaaaga aatttcctta tattaactgc | | 3315 |
| ttaatctgaa gaaagatatc tcagtacaat ctttcttcct tattctgtaa aatagtcact | | 3375 |
| tgtctgaaaa aaaaataaga gctttttttt cttaaaggct tcagaacact tagaaaggat | | 3435 |
| tacctttta agacgcgatc aagctcagat ctgcttctgt cgatggttcc tgtgaaccag | | 3495 |
| cagagcatcg cggtgggcag atagtgcaca aagcggttcc gcgttccttt actagtgaac | | 3555 |
| ctgctgatta actaaggcat ggtttttaatg tttttataaa acttgggtat gttttttaac | | 3615 |
| cttcttagtc aaatgctaga aaacccagaa tacccaattt acagtgctag aaatgcagat | | 3675 |
| taaccttgaa tcaagttcgg aatttctcag gattcctgtg ggttctctct catcgaattc | | 3735 |
| tgttgacatt tctgtttctc gtagttggtc tgctgggttc catcagcaga cacatactgc | | 3795 |

-continued

```
tgtacagcgt gtgagacatg ctgtgctgac atcagctgtt gtgactcccc gtaactccta    3855
gggtgaagtt gtgatccgtg tgtgaactaa acatttgcc cctttaggga ctcaaaaggc     3915
agcaaataca aagccacctc cttggaggat acaaaactgt ggcgttctta aacagccagt    3975
ctccgtaaga ctctaaactc cccactgctt ccggtctcat cttgccttaa gtgttatttt    4035
ttgaatatat gaatataaac atacagatga tgactggagt ggacttttaa aaatattttt   4095
tttcacaaga tactatttta ggtgaaaatg ttactgtaga tttaacagct gtttttaaagt  4155 atttgctatt attaaaactt cttcaagaac aagcgtggct atgctccac acacaggcaa    4215 tagtaacaga aagtgctcct gtttgtccac cagctcaggc aaagtacaga atggcgtttc    4275
c                                                                     4276
```

<210> SEQ ID NO 23
<211> LENGTH: 1019
<212> TYPE: PRT
<213> ORGANISM: Rat

<400> SEQUENCE: 23

```
Met Arg Asn Gly Leu Val Trp Leu Leu His Pro Ala Leu Pro Ser Thr
  1               5                  10                  15

Leu His Ser Ile Leu Gly Ala Arg Pro Pro Val Lys Arg Leu Cys
             20                  25                  30

Gly Phe Pro Lys Gln Ile Tyr Ser Thr Met Asn Asn Pro Ala Ile Gln
         35                  40                  45

Arg Ile Glu Asp His Ile Val Lys Ser Pro Glu Asp Lys Arg Glu Tyr
     50                  55                  60

Arg Gly Leu Glu Leu Ala Asn Gly Ile Lys Val Leu Leu Ile Ser Asp
 65                  70                  75                  80

Pro Thr Thr Asp Lys Ser Ser Ala Ala Leu Asp Val His Ile Gly Ser
                 85                  90                  95

Leu Ser Asp Pro Pro Asn Ile Pro Gly Leu Ser His Phe Cys Glu His
            100                 105                 110

Met Leu Phe Leu Gly Thr Lys Lys Tyr Pro Lys Glu Asn Glu Tyr Ser
        115                 120                 125

Gln Phe Leu Ser Glu His Ala Gly Ser Ser Asn Ala Phe Thr Ser Gly
    130                 135                 140

Glu His Thr Asn Tyr Tyr Phe Asp Val Ser His Glu His Leu Glu Gly
145                 150                 155                 160

Ala Leu Asp Arg Phe Ala Gln Phe Phe Leu Cys Pro Leu Phe Asp Ala
                165                 170                 175

Ser Cys Lys Asp Arg Glu Val Asn Ala Val Asp Ser Glu His Glu Lys
            180                 185                 190

Asn Val Met Asn Asp Ala Trp Arg Leu Phe Gln Leu Glu Lys Ala Thr
        195                 200                 205

Gly Asn Pro Lys His Pro Phe Ser Lys Phe Gly Thr Gly Asn Lys Tyr
    210                 215                 220

Thr Leu Glu Thr Arg Pro Asn Gln Glu Gly Ile Asp Val Arg Glu Glu
225                 230                 235                 240

Leu Leu Lys Phe His Ser Thr Tyr Tyr Ser Ser Asn Leu Met Ala Ile
                245                 250                 255

Cys Val Leu Gly Arg Glu Ser Leu Asp Asp Leu Thr Asn Leu Val Val
            260                 265                 270

Lys Leu Phe Ser Glu Val Glu Asn Lys Asn Val Pro Leu Pro Glu Phe
```

-continued

```
                275                 280                 285
    Pro Glu His Pro Phe Gln Glu Glu His Leu Lys Gln Leu Tyr Lys Ile
    290                 295                 300
    Val Pro Ile Lys Asp Ile Arg Asn Leu Tyr Val Thr Phe Pro Ile Pro
    305                 310                 315                 320
    Asp Leu Gln Gln Tyr Tyr Lys Ser Asn Pro Gly His Tyr Leu Gly His
                        325                 330                 335
    Leu Ile Gly His Glu Gly Pro Gly Ser Leu Ser Glu Leu Lys Ser
                    340                 345                 350
    Lys Gly Trp Val Asn Thr Leu Gly Gly Gln Lys Glu Gly Ala Arg
                    355                 360                 365
    Gly Phe Met Phe Phe Ile Ile Asn Val Asp Leu Thr Glu Glu Gly Leu
    370                 375                 380
    Leu His Val Glu Asp Ile Ile Leu His Met Phe Gln Tyr Ile Gln Lys
    385                 390                 395                 400
    Leu Arg Ala Glu Gly Pro Gln Glu Trp Val Phe Gln Glu Cys Lys Asp
                        405                 410                 415
    Leu Asn Ala Val Ala Phe Arg Phe Lys Asp Lys Glu Arg Pro Arg Gly
                    420                 425                 430
    Tyr Thr Ser Lys Ile Ala Gly Lys Leu His Tyr Tyr Pro Leu Asn Gly
                    435                 440                 445
    Val Leu Thr Ala Glu Tyr Leu Leu Glu Glu Phe Arg Pro Asp Leu Ile
    450                 455                 460
    Asp Met Val Leu Asp Lys Leu Arg Pro Glu Asn Val Arg Val Ala Ile
    465                 470                 475                 480
    Val Ser Lys Ser Phe Glu Gly Lys Thr Asp Arg Thr Glu Gln Trp Tyr
                        485                 490                 495
    Gly Thr Gln Tyr Lys Gln Glu Ala Ile Pro Glu Asp Val Ile Gln Lys
                    500                 505                 510
    Trp Gln Asn Ala Asp Leu Asn Gly Lys Phe Lys Leu Pro Thr Lys Asn
                    515                 520                 525
    Glu Phe Ile Pro Thr Asn Phe Glu Ile Leu Ala Leu Glu Lys Asp Ala
    530                 535                 540
    Thr Pro Tyr Pro Ala Leu Ile Lys Asp Thr Ala Met Ser Lys Leu Trp
    545                 550                 555                 560
    Phe Lys Gln Asp Asp Lys Phe Phe Leu Pro Lys Ala Cys Leu Asn Phe
                        565                 570                 575
    Glu Phe Phe Ser Pro Phe Ala Tyr Val Asp Pro Leu His Cys Asn Met
                    580                 585                 590
    Ala Tyr Leu Tyr Leu Glu Leu Leu Lys Asp Ser Leu Asn Glu Tyr Ala
                    595                 600                 605
    Tyr Ala Ala Glu Leu Ala Gly Leu Ser Tyr Asp Leu Gln Asn Thr Ile
    610                 615                 620
    Tyr Gly Met Tyr Leu Ser Val Lys Gly Tyr Asn Asp Lys Gln Pro Ile
    625                 630                 635                 640
    Leu Leu Lys Lys Ile Thr Glu Lys Met Ala Thr Phe Glu Ile Asp Lys
                        645                 650                 655
    Lys Arg Phe Glu Ile Ile Lys Glu Ala Tyr Met Arg Ser Leu Asn Asn
                    660                 665                 670
    Phe Arg Ala Glu Gln Pro His Gln His Ala Met Tyr Tyr Leu Arg Leu
                    675                 680                 685
    Leu Met Thr Glu Val Ala Trp Thr Lys Asp Glu Leu Lys Glu Ala Leu
    690                 695                 700
```

-continued

```
Asp Asp Val Thr Leu Pro Arg Leu Lys Ala Phe Ile Pro Gln Leu Leu
705                 710                 715                 720

Ser Arg Leu His Ile Glu Ala Leu Leu His Gly Asn Ile Thr Lys Gln
            725                 730                 735

Ala Ala Leu Gly Val Met Gln Met Val Glu Asp Thr Leu Ile Glu His
            740                 745                 750

Ala His Thr Lys Pro Leu Leu Pro Ser Gln Leu Val Arg Tyr Arg Glu
        755                 760                 765

Val Gln Leu Pro Asp Arg Gly Trp Phe Val Tyr Gln Arg Arg Asn Glu
    770                 775                 780

Val His Asn Asn Cys Gly Ile Glu Ile Tyr Tyr Gln Thr Asp Met Gln
785                 790                 795                 800

Ser Thr Ser Glu Asn Met Phe Leu Glu Leu Phe Cys Gln Ile Ile Ser
                805                 810                 815

Glu Pro Cys Phe Asn Thr Leu Arg Thr Lys Glu Gln Leu Gly Tyr Ile
            820                 825                 830

Val Phe Ser Gly Pro Arg Arg Ala Asn Gly Ile Gln Gly Leu Arg Phe
            835                 840                 845

Ile Ile Gln Ser Glu Lys Pro Pro His Tyr Leu Glu Ser Arg Val Glu
    850                 855                 860

Ala Phe Leu Ile Thr Met Glu Lys Ala Ile Glu Asp Met Thr Glu Glu
865                 870                 875                 880

Ala Phe Gln Lys His Ile Gln Ala Leu Ala Ile Arg Arg Leu Asp Lys
            885                 890                 895

Pro Lys Lys Leu Ser Ala Glu Cys Ala Lys Tyr Trp Gly Glu Ile Ile
            900                 905                 910

Ser Gln Gln Tyr Asn Tyr Asp Arg Asp Asn Ile Glu Val Ala Tyr Leu
        915                 920                 925

Lys Thr Leu Ser Lys Asp Asp Ile Ile Lys Phe Tyr Lys Glu Met Leu
    930                 935                 940

Ala Val Asp Ala Pro Arg Arg His Lys Val Ser Val His Val Leu Ala
945                 950                 955                 960

Arg Glu Met Asp Ser Cys Pro Val Val Gly Glu Phe Pro Ser Gln Asn
            965                 970                 975

Asp Ile Asn Leu Ser Glu Ala Pro Pro Leu Pro Gln Pro Glu Val Ile
            980                 985                 990

His Asn Met Thr Glu Phe Lys Arg Gly Leu Pro Leu Phe Pro Leu Val
        995                 1000                1005

Lys Pro His Ile Asn Phe Met Ala Ala Lys Leu
    1010                1015
```

CONGENIC ANIMAL MODELS OF NON-INSULIN DEPENDENT DIABETES MELLITUS

TECHNICAL FIELD

The invention relates to non-human congenic animals and congenic animal populations that exhibit a type II diabetes-associated phenotype, as well as insulin degradation polypeptides having substitutions that confer type II diabetes-associated phenotypes.

BACKGROUND OF THE INVENTION

Type II diabetes or non-insulin dependent diabetes mellitus (NIDDM) is an increasing health burden in urbanized societies with aging populations, as the disease is associated with older, physically inactive, overweight individuals. Approximately 135 million people worldwide are affected and therefore are at an increased risk for myocardial infarction, stroke, end-stage kidney disease, vision defects, and neurological problems.

In general, it is considered that the disease results from a combination of impaired insulin action in target tissues and a reduced capacity to secrete insulin from the pancreatic β-cells. Numerous family and twin studies have demonstrated the critical influence of environmental factors as well as a sizable impact of genetic factors for the risk to type II diabetes. Monogenic variants of diabetes with autosomal dominant mode of inheritance (MODY) or mitochondrial inheritance of disease have been described in recent years at the molecular and clinical levels. The common forms of the disease appear, however, to be multifactorial with influence of both polygenic and environmental factors.

SUMMARY OF THE INVENTION

The invention is based on the development of congenic animals and congenic animal populations that have a type II diabetes-associated phenotype. Development of congenic animal strains allows susceptibility genes residing within quantitative trait loci (QTLs) to be identified, as well as the pathophysiological implications of such genes to be characterized. As the congenic animals of the invention have a type II diabetes-associated phenotype, genetic fine mapping also can be performed, so that associated genes, such as the variant of an insulin degradation enzyme described herein, can be positionally cloned. Furthermore, physiological characterization of congenic strains and heterozygous backcross animals provides clues to the contribution of a single QTL to the pathophysiology of a complex phenotype. Niddm1 congenic strains of the invention provide specific animal models for mild type II diabetes that will allow pathophysiological mechanisms of the disease to be refined, and provide a tool for screening pharmaceutical agents.

In one aspect, the invention features a non-human congenic animal that includes genetic material of a donor animal and a recipient animal. The congenic animal exhibits a type II diabetes-associated phenotype, wherein less than about one chromosome (e.g., less than about 50 cM, 20 cM, 10 cM, or 5 cM) of the congenic animal's genome is derived from the donor animal, and wherein the genetic material from the donor is necessary for expression of the type II diabetes-associated phenotype in the congenic animal. The congenic animal can be marker-defined. Substantially all mitochondria of the congenic animal can be derived from either the recipient animal or the donor animal. The type II diabetes-associated phenotype can be selected from the group consisting of elevated postprandial glycemia, hypertension, glucose intolerance, insulin resistance, abnormal insulin secretion, reduced insulin action, increased body weight, dyslipidemia, hyperinsulinemia, impaired lipogenesis, altered glycogen metabolism, altered coagulation atherosclerosis, altered kidney function, altered nerve function, altered eye function, obesity, and inflammation.

The donor animal's genome can include a Niddm1a genomic interval. The congenic animal's genome derived from the donor can include a genomic interval selected from the group consisting of Niddm1a, Niddm1b, Niddm1c, Niddm1d, Niddm1e, Niddm1f, Niddm1g, Niddm1h, and Niddm1i. For example, the genomic interval can be a Niddm1e genomic interval. The congenic animal's genome derived from the donor also can be selected from a genomic interval selected from the group consisting of NiddmC2, NiddmC3, NiddmC5, NiddmC7, NiddmC9A, NiddmC9B, NiddmC10, NiddmC11, NiddmC13, NiddmC18, NiddmC(13+15), and NiddmC(9+13+15).

The invention also features an isolated cell of a congenic animal of the invention as well as a tissue culture derived from a congenic animal of the invention. The cell can be selected from the group consisting of adipocytes, mesangial cells, hepatic cells, pancreatic cells, muscle cells, endothelial cells, and neural cells. The tissue culture can be selected from the group consisting of adipose tissue, mesangial tissue, hepatic tissue, pancreatic tissue, muscle tissue, blood-vessel tissue, and neural tissue.

Congenic animals of the invention can be non-human mammals (e.g., a rodent such as a rat, mouse, or guinea pig, or a swine), insects, or birds. The rodent can be a rat.

The invention also features non-human congenic animal obtained by crossing a first non-human congenic animal with a second non-human congenic animal, wherein the first and second congenic animals have type II diabetes-associated phenotypes. The first and second congenic animals can have distinct metabolic phenotypes and/or have non-overlapping genomic intervals. Such congenic animals are effective for evaluating epistatic interactions between the non-overlapping genomic intervals.

In another aspect, the invention features a non-human congenic animal population that includes a plurality of non-human congenic animals. The congenic animals exhibit a plurality of type II diabetes-associated phenotypes, wherein each congenic animal within the plurality of congenic animals includes genetic material from a donor animal and a recipient animal, wherein about 0.1% to about 50% of each congenic animal's genome is derived from the donor animal, and wherein the genetic material from the donor is necessary for expression of the type II diabetes-associated phenotype in each congenic animal.

The invention also features a method for testing a pharmaceutically active compound. The method includes administering a test compound to a non-human congenic animal exhibiting a type II diabetes-associated phenotype, wherein the non-human congenic animal includes genetic material of a donor animal and a recipient animal, wherein less than about 50 cM of the congenic animal's genome is derived from the donor animal, and wherein the genetic material from the donor is necessary for expression of the type II diabetes-associated phenotype in the congenic animal; and evaluating the test compound for an effect on at least one type II diabetes-associated phenotype in the congenic animal. The congenic animal can include the genetic intervals as described above. The animal can include a progeny animal of a cross between two congenic parent animals, the parent animals having distinct congenic intervals.

In another aspect, the invention features a method for testing a pharmaceutically active compound. The method includes administering a test compound to a plurality of non-human congenic animals exhibiting a plurality of type II diabetes-associated phenotypes; and evaluating the test compound for an effect on at least one type II diabetes-associated phenotype, wherein each congenic animal within the plurality of congenic animals includes genetic material from a donor animal and a recipient animal, wherein about 0.1% to about 50% of each congenic animal's genome is derived from the donor animal, and wherein the genetic material from the donor is necessary for expression of the type II diabetes-associated phenotype in each congenic animal. The plurality of congenic animals can include at least two rats having congenic intervals on different chromosomes.

The invention also features an article of manufacture that includes isolated cells of a non-human congenic animal exhibiting a type II diabetes-associated phenotype. The article further can include a label or package insert indicating the cells are useful for evaluating compounds that may be effective for alleviating type II diabetes-associated phenotypes.

In another aspect, the invention features a method of doing business. The method includes offering for sale a non-human congenic animal exhibiting a type II diabetes-associated phenotype, or a cell derived therefrom; and communicating that the animal is effective for testing or evaluating compounds that are effective for alleviating type II diabetes-associated phenotypes.

In yet another aspect, the invention features a method of making a non-human congenic animal that includes mating a donor animal and a recipient animal to produce a progeny animal; and successively backcrossing the progeny animal with the recipient animal for at least 10 generations to produce the congenic animal, wherein the congenic animal exhibiting a type II diabetes-associated phenotype, wherein less than about 50 cM of the congenic animal's genome is derived from the donor animal, and wherein the genetic material of the donor is necessary for expression of the type II diabetes-associated phenotype in the congenic animal.

The invention also features an isolated insulin degradation polypeptide and an isolated polynucleotide encoding the insulin degradation polypeptide, wherein the polypeptide includes at least one amino acid substitution, wherein the amino acid substitution is linked to a type II diabetes-associated phenotype. The polypeptide can include at least one amino acid substitution in the amino acid sequence of SEQ ID NO:23, e.g., an arginine residue substituted at amino acid 18 and/or a valine residue is substituted at amino acid 890 of SEQ ID NO:23. The polynucleotide can have a cytosine residue at nucleotide 2817 of SEQ ID NO:22.

The invention also features a transgenic non-human animal whose genome includes an insulin-degrading polypeptide transgene, wherein the transgene includes a regulatory polynucleotide operably linked to a polynucleotide encoding an insulin-degrading polypeptide, wherein the insulin-degrading polypeptide has an amino acid substitution linked to a type II diabetes-associated phenotype. The animal can be a rat or a mouse.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIG. 3A indicates that glucose incorporation into lipids (lipogenesis) in the absence of insulin (basal conditions) was higher in F344 rats than GK (p=0.009), Niddm1b (p=0.007), and Niddm1i (p=0.04) rats. FIG. 3B indicates maximal insulin induced lipogenesis was higher in F344 than in GK (p=0.00004), Niddm1b (p=0.008), and Niddm1i (p=0.001) rats. Maximal insulin induced lipogenesis was higher in Niddm1b and Niddm1i rats compared with GK (p=0.02 and 0.006) rats. FIGS. 3C and 3D indicate dose dependent insulin stimulated lipogenesis expressed as an increase above values (mean±sem) obtained without insulin (3C) or in percent of maximum (3D).

FIG. 6A indicates that lipogenesis in the absence of insulin (basal conditions) was higher in F344 than Niddm1f (p=0.001) and Niddm1e (p=0.002) rats. FIG. 6B indicates maximal insulin induced lipogenesis was higher in F344 than in Niddm1f (p=0.00001) and Niddm1e (p=0.003) rats.

DETAILED DESCRIPTION

Figure 1:
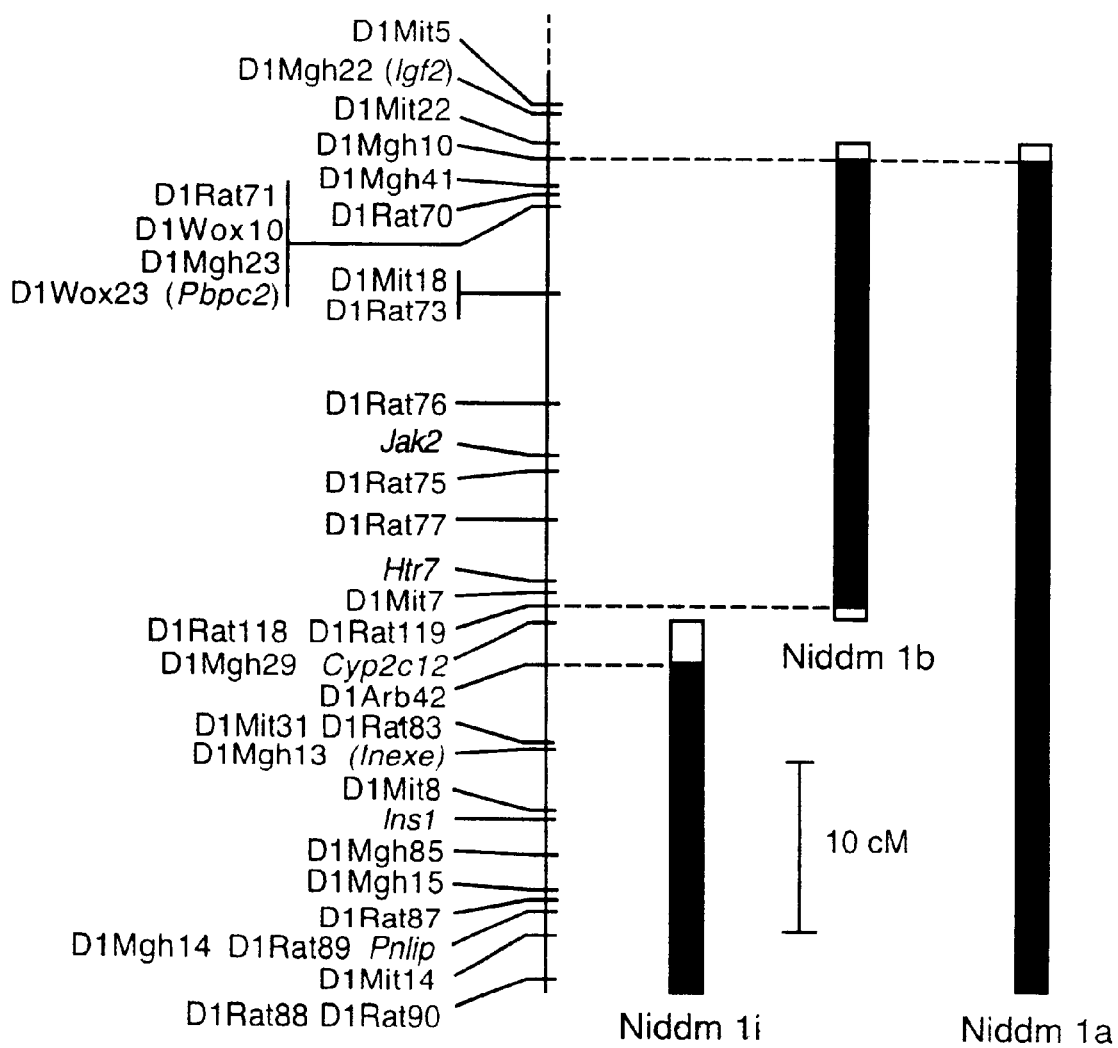
FIG. 1 is a genetic map of the distal part of rat chromosome 1 in congenic strains Niddm1a, Niddm1b, and Niddm1i. The extents of Goto-Kakizaki (GK) derived genomic intervals are displayed as black bars for the three congenic strains. White bars indicate genomic intervals spanning the crossover points between GK and F344 derived alleles, as defined by the closest flanking markers.

Congenic Animal Models of Type II Diabetes

The invention features non-human congenic animals identified following mating of a donor and a recipient animal, and cells and tissues derived from such congenic animals. In general, congenic animals contain a discrete portion of genetic material (genomic interval) from one animal strain (i.e., the donor) in the context of the genetic background of a second animal strain (i.e., the recipient). Non-human animals that are capable of being inbred are suitable for use as donor and recipient animals. Non-limiting examples include rodents such as mice, rats, rabbits, and guinea pigs, pigs, cattle, goats, fish, and birds such as turkeys and chickens. Rats, mice, and pigs are particularly useful animals. Typically, "donor" refers to an animal that has a genetically linked, type II diabetes-associated phenotype. Donor animals can be, for example, GK rats, Long-Evans Tokushima Fatty (OLETF) rats, NZO mice, and NON mice. See, for example, Kim et al., *Physiol. Pharmacol.*, 1998, 9(2–4):325-345.

The GK rat is an extensively studied animal model for type II diabetes. The phenotype of GK animals is well characterized and includes several features typical of type II diabetes, such as fasting hyperglycemia, impaired secretion of insulin in response to glucose, and insulin resistance, as well as late complications, e.g., neuropathy and nephropathy. Genetic linkage analysis of an F2-intercross between a GK and a normoglycemic F344 rat identified four major QTL with genome-wide significance (Niddm1, Niddm2, Niddm3, and weight1), as well as 10 minor QTLs that affect the segregation of diabetes and its associated phenotypes. Galli, J. et al., *Nature Genet.*, 1996, 12:31–37. OLETF rats exhibit mild obesity and develop gender dimorphic NIDDM with aging. Analysis of an F$_2$-intercross between OLETF and BN or F rats identified DmoI as a QTL associated with glucose intolerance, fasting plasma glucose levels, and body weight, and is found in the Niddm1 region of rat chromosome 1. Kim et al., 1998, supra. Typically, "recipient" refers to an inbred animal that does not exhibit a type II diabetes-associated phenotype. Recipient animals can be, for example, Fischer-344, DA, LEW, ACI, WKY, SD, or BN rats, or BALB/c, FVB, or SSL mice.

Generally, the donor animal exhibits a type II diabetes-associated phenotype while the recipient animal does not. Mating of such animals allows the type II diabetes-associated alleles to be introgressed into the context of the non-type II diabetes-associated phenotype. Alternatively, the recipient animal exhibits a type II diabetes-associated phenotype while the donor animal does not. Mating of such animals allows non-type II diabetes-associated alleles to be introgressed into the context of a type II diabetes-associated phenotype.

After mating of a donor and a recipient, progeny are successively backcrossed with recipient animals to introgress alleles of interest onto the genome of the recipient to produce congenic animals. Typically, the congenic animals are identified from at least an F10 generation. Alternatively, a procedure referred to as "speed congenics" or "marker-assisted breeding" can be used. See, for example, Whittaker et al., *Genet. Res.*, 66(3):255–265, 1995; and Darvasi, *Nat. Genet.*, 18(1):19–24, 1998. In this method, progeny in each backcross generation are chosen that have lost the maximum number of donor background alleles. Less breeding is required in this method, such that congenic animals can be identified earlier than the F10 generation (e.g., F9 generation). The phenotype of progeny can be assessed at each generation by, for example, an intraperitoneal or intravenous glucose tolerance test, in which serum glucose and insulin levels are determined in fasted animals that have been injected with glucose. In addition, insulin tolerance tests, in which the glucose levels are determined in animals after injection of insulin or tests in which nutrient or hormone levels are determined following fasting and/or provocation can be used to phenotype the animals. Substantially all the mitochondria of the congenic animals can be derived from either the donor or the recipient, as mitochondria are maternally inherited.

Genotype can be assessed in congenic animals of the invention using known genetic markers. For example, the presence of microsatellites or simple sequence length polymorphisms (SSLPs), composed of mono-, di-, tri-, or tetrameric sequences repeated multiple times in a tandem array, can be assessed by amplification of the region surrounding a microsatellite or SSLP using the polymerase chain reaction (PCR). In some embodiments, congenic animals of the invention may be characterized as "marker-defined", which indicates the animals are genetically pure when genotyped as described above. Thus, if the donor animal was a GK rat, a marker-defined congenic animal would have all markers from the recipient animal, except for a GK-specific region, which typically is less than one chromosome in length.

Thus, a major QTL such as Niddm1, which explains approximately 30% of the genetic effects on postprandial glucose concentrations, can be sorted into discrete genetic factors by establishing congenic strains covering different parts of the QTL. For example, congenic strains can be established by transferring Niddm1-GK alleles onto the genome of the normoglycemic F344 rat. The region can be less than, for example, about 50 centimorgans (cM), 20 cM, 10 cM, or 5 cM in length. As described herein, the Niddm1a, Niddm1b, Niddm1i, Niddm1e, Niddm1 d, Niddm1f, Niddm1g, and Niddm1 h congenic strains have about 52, 28, 22, 3, 19, 8, 13, and 24 cM derived from the genome of GK rats, respectively. The Niddm1 locus was dissected into two genetic entities defined by the non-overlapping congenic strains Niddm1b and Niddm1i, with each genetic entity having distinct effects on the diabetic phenotype. Congenic animals of the invention exhibit a type II diabetes-associated phenotype including one or more of the following: elevated postprandial hyperglycemia, hypertension, glucose intolerance, insulin resistance, altered insulin secretion, reduced insulin action, increased body weight, dyslipidemia, hyperinsulinemia, impaired lipogenesis, altered glycogen metabolism, altered coagulation, atherosclerosis, altered kidney function (e.g., nephropathy), altered eye function (e.g., retinopathy), altered nerve function (e.g. neuropathy), and macro- or microangiopathy. For example, congenic strains Niddm1b and Niddm1i each displayed elevated postprandial glucose levels and impaired basal and insulin induced lipogenesis in isolated adipocytes in vitro. Several features, however, are unique to the respective strains. Niddm1i rats display insulin resistance in combination with a severe reduction of insulin secretion in vivo. This substrain of the Niddm1 QTL did not develop increased body weight, epididymal fat mass, or increased levels of triglycerides. Thus, the phenotype is similar to that of patients with MODY with early defects in insulin secretion. The mode of inheritance, however, is apparently recessive since the insulin secretion defect was not observed in Niddm1i/F344 heterozygous rats. Insulin levels during IPGTT were reduced in young Niddm1i rats, although the postprandial glucose levels were barely higher than in F344, possibly indicating an important contribution of insulin independent glucose disposal at this age.

In diabetes patients, as well as in GK rats, defects in both insulin secretion and insulin action are implicated in the development of the disease. The relative etiological importance of these defects is still controversial. Since postprandial glucose levels are only slightly elevated and basal glucose is normal in 65 day old Niddm1i rats, the defects in insulin secretion and action are most likely not merely consequences of glucotoxicity. Without being bound by a particular mechanism, Niddm1i may have impaired mechanisms common to insulin secretion in pancreatic β-cells and insulin action in adipocytes. Similar to the gene encoding insulin receptor substrate 2, IRS-2, which causes defects in both insulin secretion and action in mice. Withers, D. J. et al., *Nature*, 1998, 391:900–904. The Irs-2 gene is located on chromosome 13 in humans and chromosome 8 in mice. According to syntenic conservation, the Irs-2 gene is not a candidate gene for the Niddm1i phenotype.

Young Niddm1b and heterozygous Niddm1b/F344 rats have slightly elevated postprandial glucose levels, but substantially elevated insulin levels, indicating that insulin resistance is compensated by increased insulin secretion. In older heterozygous rats, impaired insulin action can still be compensated but not in the homozygous Niddm1b rats that develop fasting hyperglycemia, fasting hyperinsulinemia, increased body weight and epididymal fat mass, as well as dyslipidemia. This constellation is well recognized in diabetes patients, in whom insulin resistance is considered as a cornerstone in the metabolic syndrome. That insulin resistance in Niddm1b rats is a likely primary defect is supported by the fact that Niddm1b/F344 heterozygous rats also exhibit signs of insulin resistance, but display normal or below normal levels of the other diabetes-associated phenotypes.

Insulin resistance and diabetes in humans are often associated with hypertriglyceridemia, increased levels of LDL cholesterol, and decreased levels of HDL cholesterol. Niddm1b rats exhibit increased triglyceride levels in combination with increased total cholesterol and HDL cholesterol. The difference between total cholesterol and HDL cholesterol should approximately reflect the LDL and VLDL cholesterol levels, for which no difference was observed between Niddm1b and F344 rats. Thus, the disordered lipid metabolism in Niddm1b does not exactly fit the pattern in diabetes patients. This discrepancy probably reflects a species-specific difference in the manifestation of dyslipidemia in rodents as compared with humans.

Data described herein indicate the presence of non-allelic interaction or epistasis between the two diabetes loci Niddm1b and Niddm1i. In Niddm1a (encompassing both Niddm1b and Niddm1i), as compared with F344 rats, the elevation of postprandial glucose levels was less severe than might be expected from the additive effect of the two sub-strains. Interpreting the epistasis in physiological terms suggests that counter-regulatory mechanisms that protect the organism against excessive glucose concentrations, restrict the hyperglycemia, unless the animals are carrying additional diabetes genes (as in GK) or are subjected to environmental stress.

The homologous chromosomal regions corresponding to Niddm1a in humans are 11q13, 9p24, and 10q24–26. Interestingly, a locus that was linked to diabetes in a Mexican-American population was recently reported on chromosome 10q. The authors also reported a locus with suggestive linkage to diabetes on human chromosome 9p, which corresponds to Niddm1b.

Additional congenic animals of the invention can be produced by crossing a first congenic animal with one or more second congenic animals. The first and second congenic animals each may be obtained from a F10 generation following a mating of a donor and recipient animal, as described above. Typically, the first and second congenic animals have non-overlapping genomic intervals derived from the donor, and typically, distinct type II diabetes-associated phenotypes. Congenic animals obtained from such crosses are effective for evaluating epistatic interactions between non-overlapping intervals.

Congenic Animal Populations

The invention features congenic animal populations that exhibit a plurality of type II diabetes-associated phenotypes. Congenic animal populations are identified from a mating of a donor and a recipient animal, as described above, but contain a plurality of animals from the F3 generation through at least the F10 generation (e.g., F12 generation). Each animal in such an animal population has from about 0.1% to about 50% of its genome derived from the donor animal. Thus, each animal in the congenic animal population has a discrete portion of its genome, which is distinct from other congenic animals in the population, derived from the donor animal.

Congenic animal populations of the invention and tissues, cells, and cellular extracts derived therefrom, are effective for evaluating epistatic effects of type II diabetes-associated phenotypes and can be used to identify pharmaceutical agents that may be useful for treating type II diabetes. For example, a test compound is administered to a congenic animal or congenic animal population of the invention, and a diabetes-associated phenotype, such as elevated postprandial hyperglycemia, hypertension, glucose intolerance, insulin resistance, altered insulin secretion, reduced insulin action, increased body weight, dyslipidemia, hyperinsulinemia, impaired lipogenesis, and altered glycogen metabolism is monitored in relation to control animals. Test compounds can be formulated into pharmaceutical compositions by admixture with pharmaceutically acceptable non-toxic excipients or carriers and administered to congenic animals of the invention by any route of administration. For example, parenteral routes such as subcutaneous, intramuscular, intravascular, intradermal, intranasal, inhalation, intrathecal, or intraperitoneal administration, and enteral routes such as sublingual, oral, or rectal administration can be used.

Insulin Degrading Polypeptides

The invention features isolated, insulin degrading enzyme (IDE) polypeptides that contain at least one amino acid substitution compared to the native polypeptide, linked to a type II diabetes-associated phenotype. As used herein, the term "polypeptide" is any chain of amino acids, regardless of length or post-translational modification. Amino acids have been designated herein by standard three letter and one letter abbreviations. Agents (e.g., small molecules or biological macromolecules) that affect IDE activity or expression can be identified with standard methodologies.

IDE is a metalloprotease that binds insulin with high specificity and a low Km, and plays an important role in cellular processing and degradation of insulin. IDE requires $Zn^{2+}$ for activity, but does not contain a typical $Zn^{2+}$ binding site, and belongs to a new class of proteases that contains an HXXEH active-site motif. The IDE protein is evolutionary well conserved, indicating that in addition to its insulin clearing function, it probably has other, more complex, cellular functions. IDE is localized in several cellular compartments including the cell surface, endosomes, cytoplasm, and peroxysomes, and is widely expressed in the body. Although insulin is the substrate with the greatest affinity for IDE, the protein interacts with several other growth factors, such as proinsulin, epidermal growth factor, and insulin-like growth factor-1 (IGF-1), that are bound but poorly degraded by IDE, and IGF-II, atrial natriuretic peptide, and transforming growth factor-α, that bind to IDE and are readily degraded. Studies also have implicated a role of IDE in other types of cellular proteolysis, as IDE has been shown to interact with the proteasome, a major site for intra-cellular protein degradation. Another implicated function for IDE is a regulatory role in steroid action, since it has been shown that IDE interacts with both the glucocorticoid and androgen receptor. See, for example, Authier et al., *Clin. Invest. Med.*, 1996, 19(3):149–160.

Modifications of the insulin-degrading polypeptide can include, for example, at least one amino acid substitution at residue 18 or 890 of the amino acid sequence of SEQ ID NO:23. The substitutions may be conservative or non-conservative. Conservative amino acid substitutions replace an amino acid with an amino acid of the same class, whereas non-conservative amino acid substitutions replace an amino acid with an amino acid of a different class. Examples of conservative substitutions include an arginine for a histidine at residue 18 (H18R) and a valine for an alanine at residue 890 (A890V) of SEQ ID NO:23. Non-conservative substitutions may result in a substantial change in the hydrophobicity of the polypeptide or in the bulk of a residue side chain. In addition, non-conservative substitutions may make a substantial change in the charge of the polypeptide, such as reducing electropositive charges or introducing electronegative charges. Examples of non-conservative substitutions include a basic amino acid for a non-polar amino acid, or a polar amino acid for an acidic amino acid.

As described herein, the Niddm1b locus was sub-mapped to a small genetic region of approximately 3.7 cM defined by congenic strain Niddm1e. The gene encoding IDE was mapped within this region, and a GK-specific allelic variant of IDE was identified. Two nucleotide variations in the translated region of the GK allele resulted in the amino-acid changes H18R and A890V. The IDE cDNA was sequenced in 12 other rat strains to investigate the frequency of the identified variants. A890V was unique for GK while the H18R was present in approximately 50% of the analyzed rat strains, indicating that the A890V variant could be of importance for the diabetic phenotype. Furthermore, in vitro expression analysis showed about a 30% reduction in insulin degradation by the GK variant containing both changes. When H18R and A890V variants were studied separately, no significant effect was observed for A890V, and H18R showed only a slightly reduced insulin degrading capacity. This indicates that the two variants are interacting synergistically to mediate the effect on insulin degradation. As the GK variants had no impact on insulin degradation in cell lysates of Ide transfected cells, the defect in IDE is specific and likely coupled to receptor-mediated internalization of insulin. It is noteworthy that the real effect of the Ide GK variant could even be larger than detected, since it is known that up to 50% of the insulin is degraded by IDE directly on the surface of cultured cells.

Nucleic Acids encoding modified insulin-degrading polypeptides

Isolated nucleic acid molecules encoding modified insulin-degrading polypeptides of the invention can be produced by standard techniques. As used herein, "isolated" refers to a sequence corresponding to part or all of a gene encoding a modified insulin-degrading polypeptide, but free of sequences that normally flank one or both sides of the wild-type gene in a mammalian genome. An isolated polynucleotide can be, for example, a recombinant DNA molecule, provided one or both of the nucleic acid sequences normally found immediately flanking that recombinant DNA molecule in a naturally-occurring genome is removed or absent. Thus, isolated polynucleotides include, without limitation, a recombinant DNA that exists as a separate molecule (e.g., a cDNA or genomic DNA fragment produced by PCR or restriction endonuclease treatment) independent of other sequences as well as recombinant DNA that is incorporated into a vector, an autonomously replicating plasmid, a virus (e.g., a retrovirus, adenovirus, or herpes virus), or into the genomic DNA of a prokaryote or eukaryote. In addition, an isolated polynucleotide can include a recombinant DNA molecule that is part of a hybrid or fusion polynucleotide.

It will be apparent to those of skill in the art that a polynucleotide existing among hundreds to millions of other polynucleotides within, for example, cDNA or genomic libraries, or gel slices containing a genomic DNA restriction digest is not to be considered an isolated polynucleotide.

Isolated polynucleotides are at least about 14 nucleotides in length and contain a substitution in the sequence from the wild-type. For example, the nucleic acid can contain a guanine at nucleotide 68, a thymine at nucleotide 2684, or a cytosine at nucleotide 2817 of SEQ ID NO:22. The nucleic acid molecule can be about 14 to 20, 20–50, 50–100, or greater than 150 nucleotides in length. In some embodiments, the isolated nucleic acid molecules encode a full-length, modified insulin-degrading polypeptide. Nucleic acid molecules can be DNA or RNA, linear or circular, and in sense or antisense orientation.

Specific point changes can be introduced into the nucleic acid molecule encoding wild-type insulin-degrading polypeptides by, for example, oligonucleotide-directed mutagenesis. In this method, a desired change is incorporated into an oligonucleotide, which then is hybridized to the wild-type nucleic acid. The oligonucleotide is extended with a DNA polymerase, creating a heteroduplex that contains a mismatch at the introduced point change, and a single-stranded nick at the 5' end, which is sealed by a DNA ligase. The mismatch is repaired upon transformation of *E. coli*, and the gene encoding the modified insulin-degrading polypeptide can be re-isolated from *E. coli*. Kits for introducing site-directed mutations can be purchased commercially. For example, Muta-Gene7 in-vitro mutagenesis kits can be purchased from Bio-Rad Laboratories, Inc. (Hercules, Calif.).

PCR techniques also can be used to introduce mutations. See, for example, Vallette et al., *Nucleic Acids Res.*, 1989, 17(2):723–733. PCR refers to a procedure or technique in which target nucleic acids are amplified. Sequence information from the ends of the region of interest or beyond typically is employed to design oligonucleotide primers that are identical in sequence to opposite strands of the template to be amplified, whereas for introduction of mutations, oligonucleotides that incorporate the desired change are used to amplify the nucleic acid sequence of interest. PCR can be used to amplify specific sequences from DNA as well as RNA, including sequences from total genomic DNA or total cellular RNA. Primers are typically 14 to 40 nucleotides in length, but can range from 10 nucleotides to hundreds of nucleotides in length. General PCR techniques are described, for example, in *PCR Primer: A Laboratory Manual*, Ed. by Dieffenbach, C. and Dveksler, G., Cold Spring Harbor Laboratory Press, 1995.

Nucleic acids encoding modified insulin-degrading polypeptides also can be produced by chemical synthesis, either as a single nucleic acid molecule or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a double-stranded nucleic acid molecule per oligonucleotide pair, which then can be ligated into a vector.

Production of modified insulin-degrading polypeptides

Modified insulin-degrading polypeptides of the invention can be produced by ligating a nucleic acid molecule encoding the polypeptide into a nucleic acid construct such as an expression vector, and transforming a bacterial or eukaryotic host cell with the expression vector. In general, nucleic acid constructs include a regulatory sequence operably linked to a nucleic acid sequence encoding an insulin-degrading polypeptide. Regulatory sequences do not typically encode a gene product, but instead affect the expression of the nucleic acid sequence. As used herein, "operably linked" refers to connection of the regulatory sequences to the nucleic acid sequence in such a way as to facilitate transcription and translation of the nucleic acid sequence. Regulatory elements can include, for example, promoter sequences, enhancer sequences, response elements, or inducible elements.

In bacterial systems, a strain of *Escherichia coli* such as BL-21 can be used. Suitable *E. coli* vectors include without limitation the pGEX series of vectors that produce fusion proteins with glutathione S-transferase (GST). Transformed *E. coli* are typically grown exponentially, then stimulated with isopropylthiogalactopyranoside (IPTG) prior to harvesting. In general, such fusion proteins are soluble and can be purified easily from lysed cells by adsorption to glutathione-agarose beads followed by elution in the presence of free glutathione. The pGEX vectors are designed to include thrombin or factor Xa protease cleavage sites such that the cloned target gene product can be released from the GST moiety.

In eukaryotic host cells, a number of viral-based expression systems can be utilized to express modified insulin-degrading polypeptides. A nucleic acid encoding an insulin-degrading polypeptide can be cloned into, for example, a baculoviral vector such as pBlueBac (Invitrogen, San Diego, Calif.) and then used to co-transfect insect cells such as *Spodoptera frugzperda* (Sf9) cells with wild-type DNA from *Autographa californica* multiply enveloped nuclear polyhedrosis virus (AcMNPV). Recombinant viruses producing the modified insulin-degrading polypeptides can be identified by standard methodology. Alternatively, a nucleic acid encoding an insulin-degrading polypeptide can be introduced into a SV40, retroviral, or vaccinia based viral vector and used to infect host cells.

Mammalian cell lines that stably express modified insulin-degrading polypeptides can be produced by using expression vectors with the appropriate control elements and a selectable marker. For example, the eukaryotic expression vector pCDNA.3.1$^+$ (Invitrogen, San Diego, Calif.) is suitable for expression of modified insulin-degrading polypeptides in, for example, COS cells, HEK293 cells, or baby hamster kidney cells. Following introduction of the expression vector by electroporation, DEAE dextran-, calcium phosphate-, liposome-mediated transfection, or other suitable method, stable cell lines can be selected. Alternatively, transiently transfected cell lines are used to produce modified insulin-degrading polypeptides. Modified insulin-degrading polypeptides also can be transcribed and translated in vitro using wheat germ extract or rabbit reticulocyte lysate.

Modified insulin-degrading polypeptides can be purified by conventional chromatography methods or chemically synthesized using standard techniques. See, Muir, T. W. and Kent, S. B., *Curr. Opin. Biotechnol.*, 1993, 4(4):420–427, for a review of protein synthesis techniques.

Transgenic Non-human Mammals

The invention also features a transgenic non-human mammal including a nucleic acid construct. As used herein, "transgenic non-human mammal" includes the founder transgenic non-human mammals as well as progeny of the founders. The nucleic acid construct includes a regulatory nucleic acid sequence operably linked to a polynucleotide encoding an insulin-degrading polypeptide, which contains at least one amino acid substitution linked to a type II diabetes-associated phenotype. Particularly useful substitutions are described above. Nucleic acid constructs can be produced through standard recombinant DNA techniques.

Transgenic non-human mammals can be farm animals such as pigs, goats, sheep, cows, horses, and rabbits, rodents such as rats, guinea pigs, and mice, and non-human primates such as baboons, monkeys, and chimpanzees. Transgenic mice are particularly useful.

Various techniques known in the art can be used to introduce nucleic acid constructs into non-human mammals to produce the founder lines of the transgenic non-human mammals. Such techniques include, but are not limited to, pronuclear microinjection (U.S. Pat. No. 4,873,191), retrovirus mediated gene transfer into germ lines (Van der Putten et al., *Proc. Natl. Acad. Sci. USA*, 82:6148, 1985), gene targeting into embryonic stem cells (Thompson et al., *Cell*, 56:313, 1989), electroporation of embryos (Lo, *Mol. Cell. Biol.*, 3:1803, 1983), and transformation of somatic cells in vitro followed by nuclear transplantation (Wilmut et al., *Nature*, 385(6619):810–813, 1997; and Wakayama et al., *Nature*, 394:369–374, 1998).

Once transgenic non-human mammals have been generated, expression of the insulin-degrading polypeptide can be assessed using standard techniques. Initial screening can be accomplished by Southern blot analysis or PCR techniques to determine whether or not integration of the transgene has taken place. See, for example, sections 9.37–9.52 of Sambrook et al., 1989, *"Molecular Cloning, A Laboratory Manual"*, second edition, Cold Spring Harbor Press, Plainview; N.Y., for a description of Southern analysis.

Expression of the nucleic acid sequence encoding an insulin-degrading polypeptide in the tissues of the transgenic non-human mammals can be assessed using techniques that include, but are not limited to, Northern blot analysis of tissue samples obtained from the animal, in situ hybridization analysis, and reverse-transcriptase PCR (RT-PCR).

The invention will be further described in the following examples, which do not limit the scope of the invention described in the claims.

EXAMPLES

Example 1

Materials and Methods: Inbred Fischer-344 (F344) rats were purchased from Charles River Laboratories and maintained by brother-sister mating. Rats had free access to tap water and chow and were maintained at a 12-h light and dark cycle (6 am/6 pm). Certain rats were fed a high fat diet containing 2% cholesterol, 20% olive oil, and 0.5% bile acid mixed in standard chow, starting at an age of 120 day.

Rat strain GK was obtained and bred as described by Galli et al., *Nature Genet.*, 1996, 12:31–37. GK-derived genetic intervals were transferred onto the F344 genetic background by 10 successive backcrosses (F10) followed by intercrosses between heterozygous animals to establish homozygous congenic strains. At each generation, genetic markers from the Niddm1 region were used to verify the integrity of the GK-susceptibility haplotype. The Niddm1e, Niddm1f, and Niddm1c congenic strains were bred by 12 successive backcrosses to F344 followed by intercrosses to establish homozygous lines.

Intraperitoneal glucose tolerance test: Intraperitoneal glucose tolerance tests (IPGTT) were performed on male rats of 95 and 225 days of age, as described by Galli et al., 1996, supra. Animals were fasted for 6–7 h; blood glucose levels were measured at 0 (baseline), 15, 30, 60, and 90 min after injection of 2.0 g glucose per kg body weight; and serum immunoreactive insulin levels were determined at 0, 15, and 30 min. Serum insulin levels in Tables 1, 2, and 3 were determined by an ELISA for rat insulin (Mercodia A B, Uppsala, Sweden), as described by the manufacturer. Insulin values ($\mu$g/l) obtained from the ELISA analysis were converted to pmol/l by multiplying by a factor of 174. The area under the curve (AUC) was calculated according to the trapezoid rule from glucose measurements at baseline, 15, 30, 60, and 90 min (mmol/l×min). Glucose and insulin values presented in FIG. 2 were standardized by division with the corresponding mean values of F344 and subsequently multiplied by the mean values of F344 that are presented in Table 2. The glucose mean values of F344 in the experiment presented in FIG. 2 are: 5.0 (basal), 18.6 (15 min), 13.8 (30 min), 6.6 (60 min), and 6.2 mmol/l (90 min). The corresponding insulin mean values are: 63 (basal), 200 (15 min), and 215 pmol/l (30 min).

Lipid analysis: Serum levels of triglycerides, total cholesterol, and HDL cholesterol were determined with Vitros TRIG Slides, Vitros CHOL Slides (Johnson & Johnson Clin. Diagn. Inc., USA), and Liquid N-geneous HDL-c reagent kit (Biomed-RK, Jönköping, Sweden), respectively.

Lipogenesis and Lipolysis: Male rats (75 days) were decapitated after carbon dioxide anesthesia, and epididymal fat depots (1–2 g) were removed. Adipocytes were prepared as described by Kamel et al., *Pediatr. Res.*, 1997, 41:563–567. Studies of glucose incorporation into lipids (lipogenesis) were performed at a glucose concentration of 1 $\mu$M, at which glucose transport into the cells is rate limiting. Adipocytes were incubated at 2% (v/v) concentration in 0.5 ml Krebs Ringer phosphate buffer (KRP) containing 40 mg/ml albumin (Sigma Chemical Co., St. Louis, Mo.), 0.2 $\mu$M [$^3$H]-glucose (5×10$^6$ cpm), 1.0 $\mu$M unlabeled glucose, and insulin at the indicated concentrations. At each insulin concentration, the analysis was performed in triplicate at 37° C. for 2 h, and the reactions were terminated by rapid chilling to 4° C. Incorporation of glucose into lipids was determined, as described by Moody et al., *Horm. Metab. Res.*, 1974, 6:12–16, by mixing 45 $\mu$l of 6.0 M H$_2$SO$_4$ and 4.0 ml of toluene with 2,5-diphenyloxazole (PPO) and adding to each vial containing adipocytes. Vials were left at room temperature overnight before liquid scintillation counting. For characterization of lipolysis, adipocytes were incubated for 2 h at 37° C. in KRP buffer containing 40 mg/ml albumin (Sigma) and 5.6 mmol/l glucose. The final adipocyte suspension was 1% (v/v). At the end of the incubation, an aliquot of the medium was removed for analysis of glycerol release, which was used as an index of lipolysis. To assess maximal lipolysis, noradrenaline (1 nmol/l to 0.1 mmol/l) was added to the incubation media. Lipogenesis and lipolysis were expressed per cell surface area in order to eliminate differences solely depending on adipocyte size. Maximal insulin induced lipogenesis was calculated as the difference between glucose incorporation at maximum minus the incorporation of glucose in the absence of insulin. Maximal noradrenaline induced stimulations of lipolysis (responsiveness) were calculated from each individual dose-response curve as the maximum glycerol release minus glycerol release in the absence of noradrenaline. The concentration of noradrenaline or insulin that produced 50% of the maximum effect (EC$_{50}$, sensitivity) was calculated from the individual dose-response curves.

Insulin mRNA analysis: RNA levels of the rat insulin genes, Ins1 and Ins2, in pancreas were determined by semi-quantitative RT-PCR. Five-months old male rats were fasted for 7 h and pancreas were isolated directly or after glucose challenge. In the latter case, glucose (2 g/kg and subsequently 1 g/kg body weight) was injected intraperitoneally at 0 and 60 min, and the rats were sacrificed at 120 min. Total pancreatic RNA (0.75 $\mu$g) was reverse transcribed in a total volume of 20 $\mu$l, using BRL Superscript II (Life Technologies), as described by the manufacturer. The two transcripts from Ins1 and Ins2 were reverse transcribed with a primer common to both insulin genes (5'TTTATTCATTGCAGAGGGGT-3', SEQ ID NO:1). The cDNA reaction (5 $\mu$l) was directly introduced into a 25 $\mu$l PCR solution containing Dynazyme DNA polymerase and buffer (Finnzymes Oy). Ins1 and Ins2 genes were amplified in separate reactions with $^{32}$P labeled specific primers (Ins1 primers: 5'-GTGACCAGCTACAATCATAG-3', SEQ ID NO:2, and 5'-GTGCCAAGGTCTGAAGATCC-3', SEQ ID NO:3; Ins2 primers: 5'GTGACCAGCTACAGTCGGAA-3', SEQ ID NO:4, and 5'GTGCCAAGGTCTGAAGGTCA-3', SEQ ID NO:5) by denaturation at 94° C. for 3 min, followed by 20 cycles consisting of denaturation at 94° C. for 30 s, annealing at 62° C. for 30 s, and extension at 72° C. for 1 min, with a final extension for 7 min at 72° C. Insulin specific products accumulated exponentially up to cycle 24. Samples (15 $\mu$l) were separated on 6% polyacrylamide gels, which were dried and the radioactivity visualized and quantified by phosphorimager analysis (Fujix BAS 1000).

Genotype analysis and localization of markers: Rats were genotyped by PCR amplification of microsatellite markers as previously described by Jacob, H. J. et al., *Cell*, 1991, 67:213–224, with the exception that $^{33}$P-$\gamma$ATP was used to label one primer in each pair. For the genetic mapping of new markers, 45 rats with the most extreme glucose values from the first F2 intercross of GK and F344 rats were genotyped, and markers were placed on a genetic map using the computer package Mapmaker/exp 3.0.

Generation of new RFLP markers and Southern blot analysis: Hybridization probes were synthesized by RT-PCR or genomic PCR, using available rat cDNA sequences and gene specific primers. Total RNA was prepared as previously described. Six μg of RNA was transcribed using BRL Superscript II (Life Technologies), as described by the manufacturer. For the Jak2 probe, total RNA prepared from the whole body of a 1 day old rat was used in the reverse transcriptase reaction (cDNA primer: 5'-AAGGGCCCGTGGACACGAG-3', SEQ ID NO:6) and 2 μl of the reverse transcriptase reaction was introduced in the subsequent PCR amplification primers: 5'AAGGGCCCGTGGACACGAG-3', SEQ ID NO:6, and 5'GAAGAGCAAAAGCCCACCTG-3', SEQ ID NO:7), using a PCR-profile of denaturation at 96° C. for 4 min, followed by 35 cycles consisting of denaturation at 96° C. for 30 s, annealing at 55° C. for 1 min, extension at 72° C. for 2 min, and a final extension for 7 min at 72° C. The jak2 gene was mapped by a HindIII RFLP with fragment lengths of 8.6 kb in GK and 6.4 kb in F344. Pnlip mRNA from total pancreatic RNA was reverse transcribed using a primer having the nucleotide sequence of 5'-ACTACAGAAGTTGAACACTCTG-3' (SEQ ID NO:8). PCR conditions were identical to the jak2 reaction, except that an annealing temperature of 50° C. was used (primers: 5'-CGATGCCCAGTTTGTGGATG-3', SEQ ID NO:9, and 5'-ACTACAGAAGTTGAACACTCTG-3', SEQ ID NO:10). One μl from the first amplification was used as template in a second nested PCR (primers: 5'-ACTTAGGATTTGGAATGAGC-3', SEQ ID NO:11 and 5'TTGGGTAGAGTTGGGTTGAT-3', SEQ ID NO:12; conditions as for Jak2, except that annealing was performed at 53° C.). A StuI RFLP was used to genetically map the Pnlip gene with fragments of 18 kb in GK and 14 and 4 kb in F344. The Htr7 gene was amplified by genomic PCR at the same conditions as for Pnlip (primers for first PCR amplification: 5'-CGAAATCATTGGCTGAGACTG-3', SEQ ID NO:13 and 5'GGGTACTCTTCTGAACTGTGG-3', SEQ ID NO:14; second nested PCR primers: 5'TGGCTTCTGTCTTCTTCTTGG-3', SEQ ID NO:15 and 5'CTGCTTCCTTACCTGTCCTTA-3', SEQ ID NO:16). An MspI RFLP was identified for Pnlip that generated fragments of 5.5 kb for GK and 4.5 kb for F344. Southern blot analysis was performed with high molecular weight DNA that was extracted from rat liver and digested (10 μg) with the appropriate restriction endonuclease. After fractionation in 0.8% agarose gels and transfer to a nylon membrane (Zeta-probe, Bio-Rad), $^{32}$Pγ-labeled RFLP probes (random priming) were used to probe the membrane.

Genetic mapping of Ide: The Ide probe for hybridization was synthesized by RT-PCR, using available rat cDNA sequences (GenBank Accession No. X67269 S53969) and gene specific primers. For the reverse transcriptase reaction, total RNA was prepared from the whole body of a 1 day old rat, as described above. Six μg of RNA was transcribed in a total volume of 20 μl using BRL Superscript II (Life Technologies), as described by the manufacturer. IDE mRNA was reverse transcribed with a primer having the nucleotide sequence 5'-AGCTGGTGGACAAACAGGAG-3', (SEQ ID NO:17) and 2 μl of the reverse transcriptase reaction was introduced in the subsequent PCR amplification (primers: 5'GTGAACCTGCTGATTAACTAAG-3', SEQ ID NO:18, and 5'AGCTGGTGGACAAACAGGAG-3', SEQ ID NO:17). The PCR-profile that was used included denaturation at 94° C. for 4 min and 30 cycles consisting of 94° C. for 30 sec, annealing at 55° C. for 1 min, and extension at 72° C. for 2 min, with a final extension for 7 min at 72° C. Southern blot analysis was performed as described above. A HincII RFLP was identified that generated fragments of 2.7 kb in GK and 0.7 kb in F344.

Sequencing of rat IDE cDNA: A 3128 bp rat Ide cDNA fragment that was amplified by RT-PCR with gene specific primers, was sequenced. Six μg of total RNA prepared from rat liver was used in a 20 μl reverse transcriptase reaction with a cDNA primer having the nucleotide sequence of 5'-CTGTTTGTCTCTCTAATTGC-3' (SEQ ID NO:19). Two μl of the reverse transcriptase reaction was introduced in the PCR reaction, using Expand Long Template PCR System (Boehringer Mannheim) as described by the manufacturer (PCR primers: 5'-ATGCGGAACGGGCTCGTGTG-3', SEQ ID NO:20, and 5'AGCCAGAAACTACTCAAAGC-3', SEQ ID NO:21, using a PCR profile of 94° C. for 2 min, and 30 cycles consisting of 94° C. for 10 sec, 54° C. for 30 sec, 68° C. for 2.5 min, of which the last 20 cycles were elongated for 20 sec at 68° C. for each cycle, and a final extension for 7 min at 68° C.). The DNA sequences of the RT-PCR products were determined using ABI PRISM BigDye Terminator Cycle Sequencing Ready Reaction kit and Ide specific primers in an ABI PRISM 377 semi-automatic sequencer (Applied Biosystems, USA).

Plasmid construction and COS1 cell transfections: Ide mRNA from GK and F344 was amplified by RT-PCR, as described above, with primers extended with restriction sites. The resulting 3.1 kb cDNA product containing the complete translated region, was ligated into BglII and MluI restriction sites of expression vector pCMV4 (D. W Russel, Dept. of Mol. Gen., University of Texas Southwestern Medical center), under control of the cytomegalovirus promoter. The Ide cDNA inserts in the resulting constructs pCMV4-Ide(GK) and pCMV4-Ide(F344) were sequenced to exclude PCR artifacts. Internal restriction sites were used to separate the GK sequence variants generating pCMV4-Ide (H18R) and pCMV4-Ide(A890V). Approximately 6×10$^6$ COS-1 cells were transiently transfected by electroporation (Bio-Rad Gene Pulser, Richmond, Calif.; 1200 V, 25 μF) with 10 μg of pCMV4-Ide plasmid together with 1 μg of the β-galactosidase vector pCH110 (Pharmacia, Sweden).

Assay of insulin degrading activity: Transfected COS-1 cells were seeded in 6 cm petri dishes, and incubated for 36 h in Dulbecco's modified Eagles medium (DMEM) supplemented with 10% calf serum. Subsequently, the cells were washed twice in PBS, preincubated at 37° C. in 3 ml DMEM supplemented with 1 mg/ml BSA for 30 min, and incubated in 2 ml DMEM containing 1 mg/ml BSA and 15,000 cpm/ml of $^{125}$I-insulin (ratio of labeled to unlabeled insulin was 1:150). Triplicate aliquots of 100 μl were removed at 30, 45, and 60 min, after addition of insulin, and undegraded insulin was precipitated for 30 min on ice with one volume of 25% TCA. Samples were centrifuged at 14,000 rpm for 20 min, the supernatant recovered, and the amount of undegraded insulin measured by radioactive accounting. Cells were further washed two times with PBS, incubated for 2 hours in DMEM, trypsinized, and washed 3 times in PBS. The cells (approximately 3×10$^6$ cells per plate) were recovered for homogenization by sonication for 15 sec in 300 μl of 100 mM phosphate buffer (pH=7.4) containing 0.5 mg/ml BSA. The homogenate was centrifuged at 350 g for 10 min, and the supernatant was collected for measurement of insulin degradation activity, protein concentration (Bradley ANDREJ), β-galactosidase activity (Maniatis ANDREJ), and Western blot analysis. Triple aliquots of cell lysates containing 1 μg protein were incubated for 15 min at 37° C. in 100 μl of assay buffer containing 2,000 cpm of $^{125}$I insulin, and the amount of degraded insulin were measured as above. In all experiments background COS1 insulin degrading activity (in cells transfected with pCMV plasmid)

was 20 to 25% of cells expressing wild type rat IDE. The IDE protein was detected by immunoblotting according to standard procedures using IDE antibodies kindly provided by Dr. M. R. Rosner (ANDREJ Adress).

Example 2

Characterization of Niddm1 sub-loci: A breeding protocol was established to allow for the transfer of the GK-Niddm1 diabetes susceptibility allele onto the background genome of the normoglycemic F344 rat. A long interval was transferred from GK to F344 to assure that no susceptibility genes in this chromosomal region were lost (FIG. 1). The GK-specific region in the congenic strain F344.GK-Niddm1a (Niddm1a) was 52±3 cM long and contained the complete 20 cM 95% confidence interval previously defined for Niddm1 flanked by approximately 15 cM of additional GK alleles. A number of sub-strains were produced from Niddm1a to define the location of the Niddm1 susceptibility gene/genes. Two of these strains, F344.GK-Niddm1b (Niddm1b) and F344.GK-Niddm1i (Niddm1i), retained 28±1 cM and 22±1 cM of the GK interval. The GK regions in Niddm1b and Niddm1i are distinct and non-overlapping since two markers (Cyp2c12 and D1Mgh29), separating the two GK regions, are homozygous for F344 alleles (FIG. 1). All congenic strains were passed through 10 successive generations of backcrossing to obtain genetically pure animals. To verify the purity of the strains, a genome-wide analysis was performed with 111 markers spaced at an average of 20 cM. Special care was taken to analyze known loci for diabetes-associated phenotypes. No remaining GK derived alleles were found.

Figure 2A:
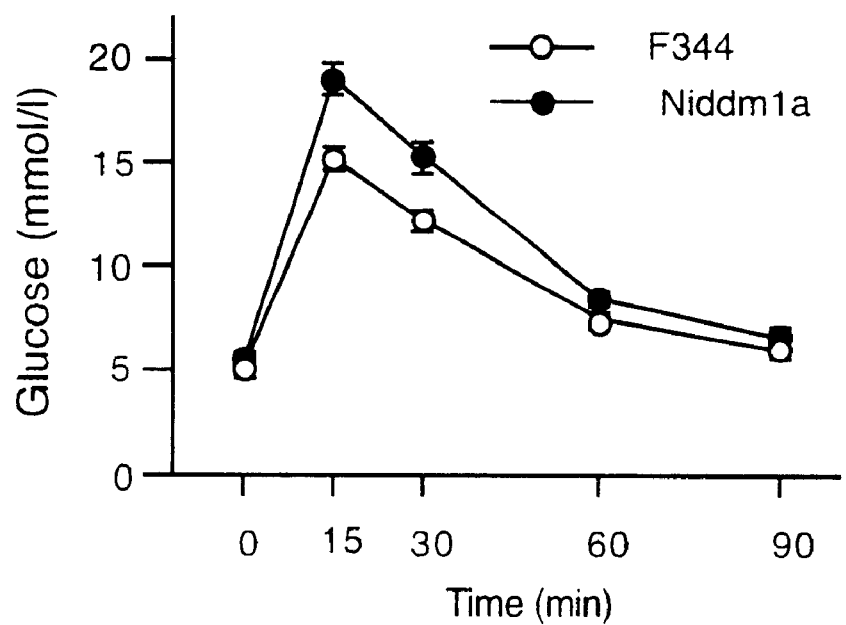
FIGS. 2A–2D are graphs that depict intraperitoneal glucose tolerance test results of Niddm1 congenics and F344 rats. Male rats (95 days) from strains Niddm1a (n=11), Niddm1b (n=17), Niddm1i (n=12), and F344 (n=20) were subjected to IPGTT. After glucose injection, the concentrations of blood glucose (2A, 2B) and serum insulin (2C, 2D) were determined at the indicated time points. Results are shown as mean±sem.

The IPGTT was used to identify the Niddm1 locus in the original F2-intercross and also applied to characterize the congenic strains. To challenge further the animals, the IPGTT was performed in older rats (95 days compared with 70 days). Niddm1a rats with the complete Niddm1 chromosome region (52 cM) differed significantly from F344 rats in glucose tolerance during IPGTT (FIG. 2A). As compared with F344, the glucose AUC were significantly higher in Niddm1a (p=0.0007), Niddm1b (p=0.002), and Niddm1i (p=0.00001). The serum insulin levels at 15 and 30 min were significantly lower in Niddm1i than in F344 (p=0.01 and 0.002). No differences in body weight were observed in this experiment when comparing Niddm1a, Niddm1b, or Niddm1i with F344 rats. The most pronounced difference was observed 15 min after glucose injection, when the mean glucose concentration in Niddm1a was 4.0 mmol/l (26%) higher than in F344 (p=0.0005). Also, the two congenic strains carrying separate parts of the Niddm1 locus, displayed significantly higher postprandial glucose concentrations compared with control F344 rats.

Figure 2B:
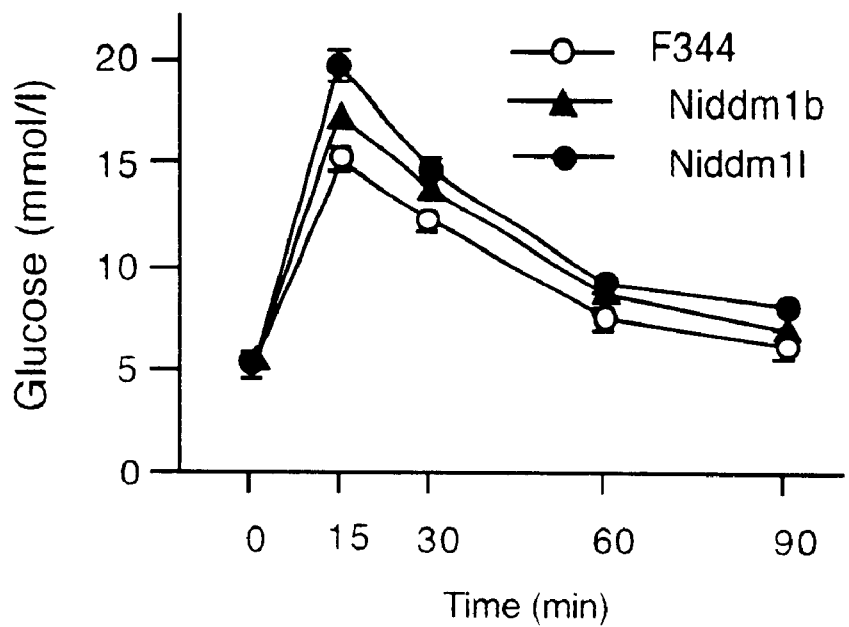

The results of the IPGTT of Niddm1b and Niddm1i compared with the control F344 rat are shown in FIG. 2B. At 15 min following glucose injection, Niddm1b and Niddm1i rats exhibited 2.3 mmol/l (15%) and 4.7 mmol/l (31%) higher glucose levels than F344 (p=0.008 and p=0.00005). The sum of the AUC increases over F344 for the two sub-strains (Niddm1b and Niddm1i) were distinctly larger than the AUC increase of the parental strain (Niddm1a). The sum AUCs of Niddm1b and Niddm1i was 325, compared to 171 in Niddm1a, clearly indicating that non-allelic interaction (epistasis) is operating within the Niddm1 locus.

Figure 2C:
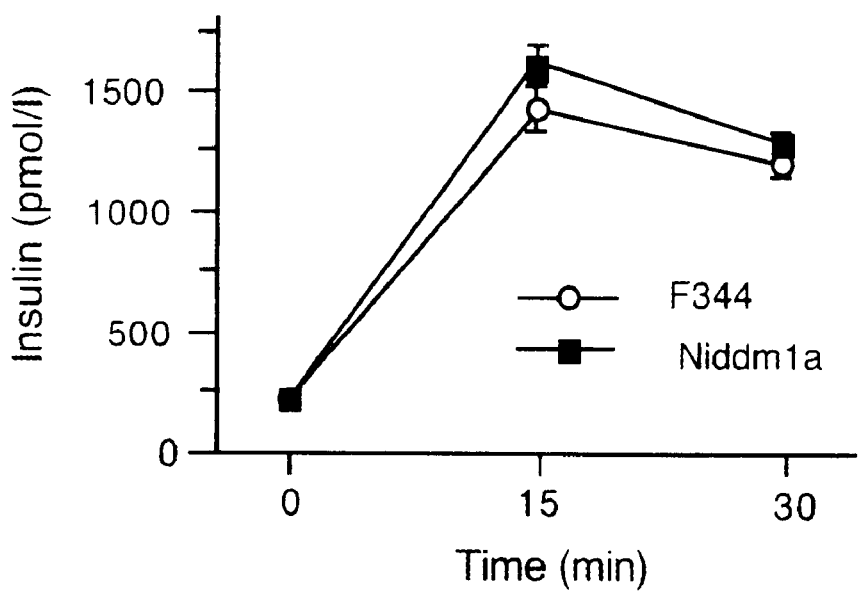
Figure 2D:
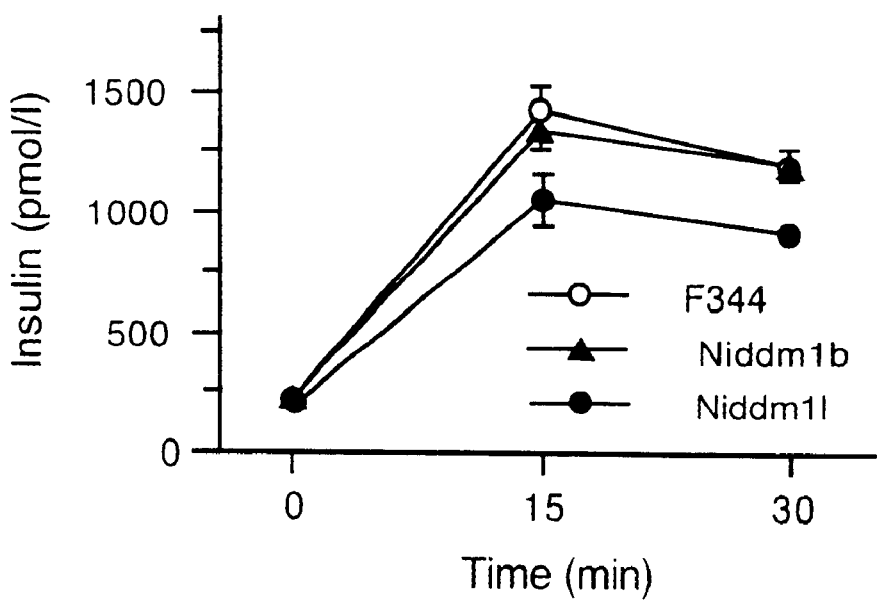
Figure 3A:
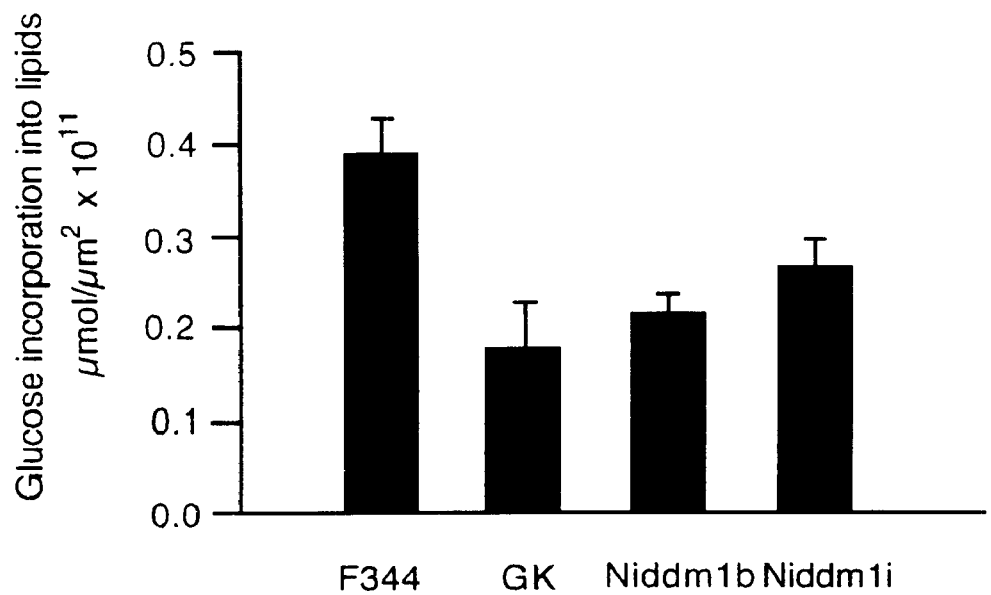
FIGS. 3A-3D are graphs that depict glucose incorporation into lipids as a result of insulin stimulated synthesis in F344, GK, Niddm1b, and Niddm1i rats. Adipocytes were isolated from epididymal fat of two month old male F344 (n=7), GK (n=4), Niddm1b (n=5), and Niddm1i (n=5) rats, and incubated for 2 h with insulin (0–20,000 $\mu$U/ml).
Figure 3B:
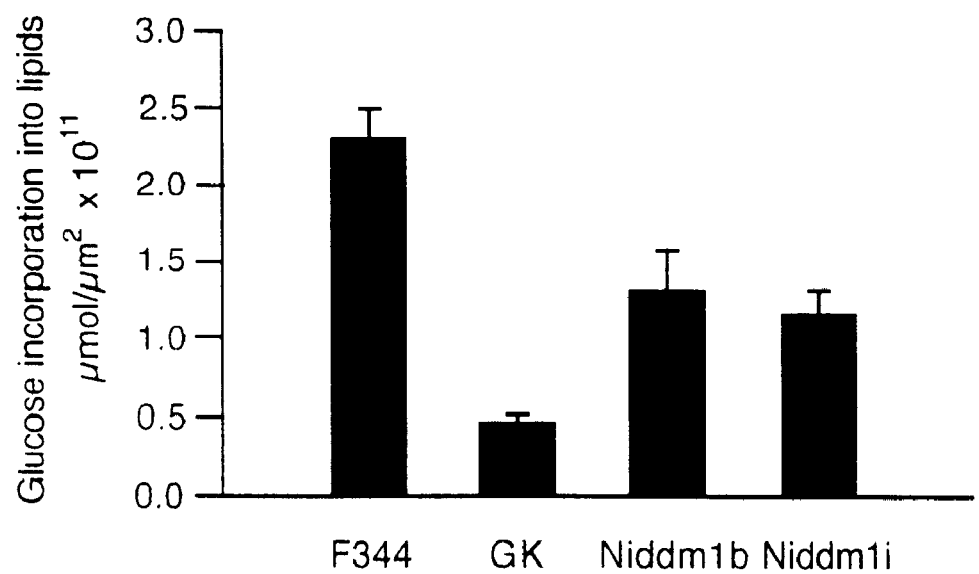
Figure 3C:
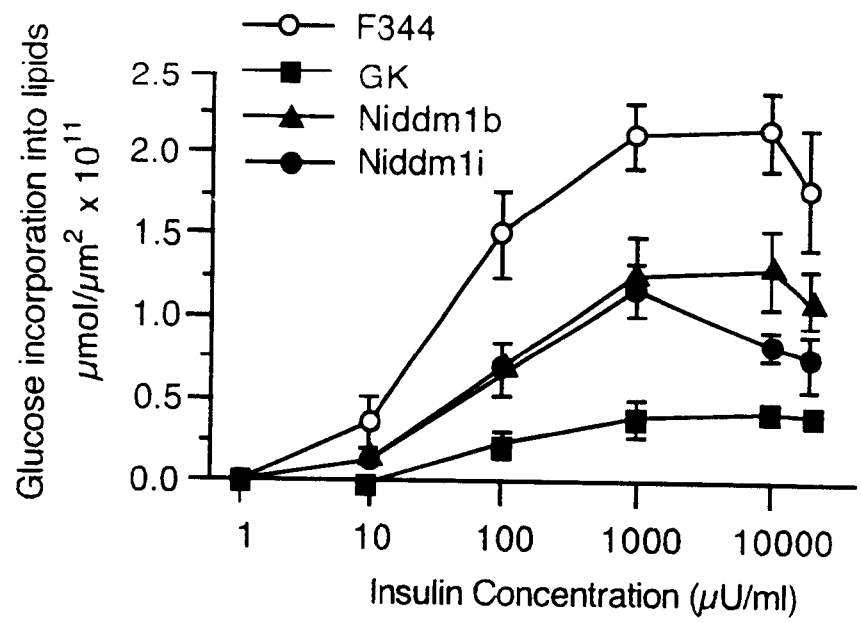
Figure 3D:
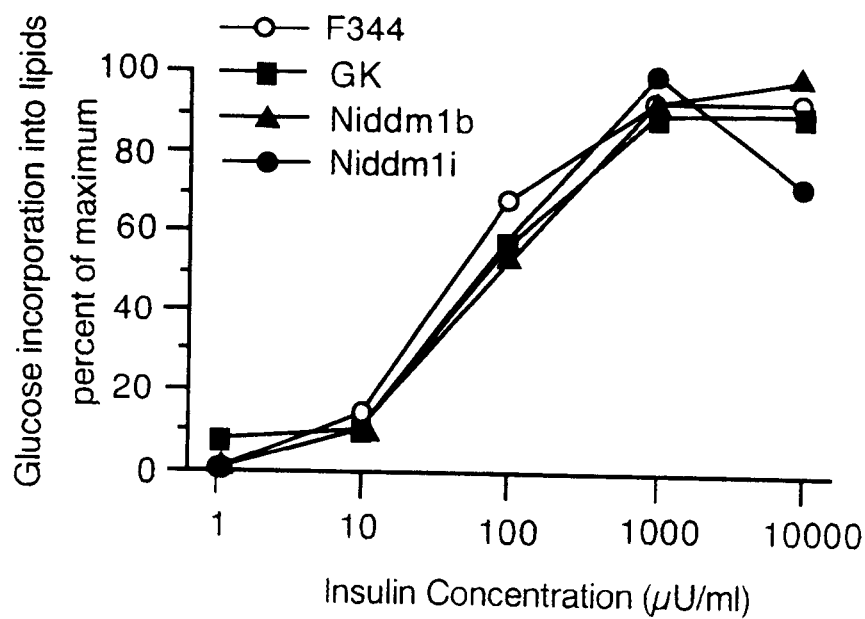

A discriminating feature of Niddm1i in comparison with Niddm1b was the significantly lower serum insulin levels at 15 and 30 min (p=0.03 and p=0.002). At 15 and 30 min post-injection, the insulin values in Niddm1i were 385 pmol/l (27%, p=0.012) and 294 pmol/l (24%, p=0.002) lower than in F344 (FIG. 2D). No significant differences in insulin levels were observed when comparing either Niddm1a or Niddm1b with F344 (FIGS. 2C and D). It appears that the Niddm1 locus contains at least two separate genes affecting glucose homeostasis, since the Niddm1i and Niddm1b both affect glucose levels but cover different parts of chromosome 1 and display major differences in glucose stimulated insulin secretion in vivo.

Example 3

Diabetes development in Niddm1b and Niddm1i: To further investigate the diabetes phenotype associated with the GK alleles at the Niddm1b and Niddm1i loci, congenic rats were studied at different ages in a prospective study. In order to characterize the phenotypic effects of each GK-allele at the loci, GK/F344 heterozygous animals also were studied. The heterozygous animals were produced by backcrossing of Niddm1b or Niddm1i to F344. These animals were denoted Niddm1b/F344 and Niddm1i/F344, to indicate the heterozygous nature at each locus. Male rats carrying the Niddm1b or Niddm1i locus in homozygous (GK/GK) or heterozygous (GK/F344) form and F344 rats were subjected to IPGTT at 65 and 95 days of age. At 185 days of age, the basal levels of blood glucose, serum insulin, triglyceride, total cholesterol, and HDL cholesterol were determined; subsequently the animals were sacrificed, and the epididymal fat depots were weighed.

At 65 days of age, Niddm1b and Niddm1b/F344 showed slightly elevated postprandial glucose levels (mmol/l) at the early time points (15 and 30 min) during the IPGTT as compared to F344 rats (Table 1). However, the basal and 30 min serum insulin levels (pmol/l) were significantly higher in Niddm1b and Niddm1b/F344 (Table 1).

TABLE 1

Diabetes-associated phenotypes in Niddm1 congenics and F344 at age 65 days

| Phenotype | F344 (n = 15) | Niddm1b/F344 (n = 12) | Niddm1b (n = 11) | Niddm1i/F344 (n = 8) | Niddm1i (n = 11) |
| --- | --- | --- | --- | --- | --- |
| Weight (g) | 207 ± 3 | 216 ± 4 | 228 ± 4*** | 202 ± 4 | 197 ± 5 |
| Glucose 0 min | 4.8 ± 0.1 | 4.6 ± 0.1 | 4.8 ± 0.1 | 4.6 ± 0.2 | 4.7 ± 0.1 |
| Glucose 15 min | 15.9 ± 0.4 | 17.0 ± 0.5 | 17.3 ± 0.6* | 15.4 ± 1.0 | 17.2 ± 0.5* |
| Glucose 30 min | 9.4 ± 0.3 | 10.3 ± 0.4 | 10.6 ± 0.5* | 8.2 ± 0.7 | 10.5 ± 0.4* |
| Glucose 60 min | 4.9 ± 0.2 | 5.2 ± 0.3 | 5.5 ± 0.2 | 6.0 ± 0.1** | 4.9 ± 0.1 |
| Glucose 90 min | 4.8 ± 0.2 | 5.2 ± 0.2 | 5.1 ± 0.1 | 5.6 ± 0.2* | 4.8 ± 0.2 |
| Glucose AUC | 705 ± 12 | 755 ± 18* | 774 ± 20** | 712 ± 26 | 748 ± 18 |

TABLE 1-continued

Diabetes-associated phenotypes in Niddml congenics and F344 at age 65 days

| Phenotype | F344 (n = 15) | Niddm1b/F344 (n = 12) | Niddm1b (n = 11) | Niddm1i/F344 (n = 8) | Niddm1i (n = 11) |
| --- | --- | --- | --- | --- | --- |
| Insulin 0 min | 77 ± 7 | 109 ± 9** | 122 ± 22* | 78 ± 10 | 62 ± 18 |
| Insulin 15 min | 1,234 ± 182 | 1,259 ± 178 | 1,263 ± 143 | 1,111 ± 163 | 542 ± 76** |
| Insulin 30 min | 498 ± 68 | 857 ± 64 | 980 ± 153** | 351 ± 74 | 398 ± 68 |

All values are given as mean ± standard error of the mean (sem).
Each congenic strain was compared with F344 (Student = s T-test) and significant differences are indicated: *P < 0.05, P < 0.01, *P < 0.001.

Basal insulin levels (pmol/l) in Niddm1b and Niddm1b/F344 were 58% and 42% higher compared with F344 and at 30 min post-injection, the corresponding increases were 97% and 72%. In concordance with the experiment shown in FIG. 2, postprandial glucose levels (mmol/l) in mid-aged (95 days) Niddm1b rats were significantly higher than in F344 (Table 2).

TABLE 2

Diabetes-associated phenotypes in Niddml congenics and F344 at age 95 days

| Phenotype | F344 (n = 15) | Niddm1b/F344 (n = 12) | Niddm1b (n = 11) | Niddm1i/F344 (n = 8) | Niddm1i (n = 11) |
| --- | --- | --- | --- | --- | --- |
| Weight (g) | 279 ± 4 | 280 ± 4 | 305 ± 5*** | 275 ± 4 | 270 ± 6 |
| Glucose 0 min | 5.1 ± 0.1 | 4.9 ± 0.1 | 5.6 ± 0.3 | 5.3 ± 0.1 | 5.8 ± 0.2** |
| Glucose 15 min | 15.1 ± 0.5 | 15.4 ± 0.6 | 17.4 ± 0.7** | 16.6 ± 1.1 | 18.5 ± 0.8*** |
| Glucose 30 min | 12.2 ± 0.3 | 12.2 ± 0.5 | 14.1 ± 0.7** | 13.1 ± 0.4 | 14.0 ± 0.4*** |
| Glucose 60 min | 7.5 ± 0.3 | 7.2 ± 0.3 | 8.1 ± 0.5 | 7.3 ± 0.3 | 8.5 ± 0.3* |
| Glucose 90 min | 6.1 ± 0.2 | 6.0 ± 0.2 | 7.1 ± 0.2** | 6.6 ± 0.2 | 7.2 ± 0.2*** |
| Glucose AUC | 855 ± 21 | 846 ± 29 | 971 ± 35** | 901 ± 31 | 1001 ± 28*** |
| Insulin 0 min | 210 ± 27 | 208 ± 23 | 238 ± 80 | 260 ± 38 | 225 ± 48 |
| Insulin 15 min | 1,425 ± 205 | 1,589 ± 141 | 1,166 ± 287 | 1,787 ± 142 | 810 ± 193* |
| Insulin 30 min | 1,200 ± 186 | 1,507 ± 138 | 1,141 ± 297 | 1,563 ± 168 | 792 ± 189 |

All values are given as mean " standard error of the mean (sem).
Each congenic strain was compared with F344 (Student's T-test) and significant differences are indicated: *P < 0.05, P < 0.01, *P < 0.001.

No difference in glucose levels was observed between Niddm1b/F344 and F344. At this age, the serum insulin levels in the heterozygous animals were still slightly higher (15 and 30 min). In contrast, a slight insulin decrease was observed in the homozygous animals (Table 2). Although, the insulin levels in Niddm1b were not significantly different from F344 during IPGTT, insulin secretion was impaired in light of the increased glucose levels.

Later in life (185 days), both basal glucose and basal insulin levels in Niddm1b were significantly higher than in F344 rats (Table 3). The levels of triglyceride and HDL cholesterol also were significantly higher in Niddm1b than in F344 rats (Table 3), while the total cholesterol levels were not different. In contrast to the cholesterol levels in Niddm1b rats, both total cholesterol and HDL cholesterol levels in the heterozygous rats (Niddm1b/F344) were significantly lower than in F344 rats. No differences in basal glucose, insulin, or triglyceride levels were found between Niddm1b/F344 and F344. Moreover, the Niddm1b rats were significantly heavier (10%, 9%, and 6%, at 65, 95, and 185 days, respectively) than F344 rats in this experimental series (Table 1–3), and the epididymal fat weight was increased by 18% (Table 3). The increase in Niddm1b body weight was not observed in the first experiment, the possibility that this reflects merely a consequence of differences in nutrition during early life can not be excluded. Genetic linkage to body weight, however, was observed in the original genetic analysis of the GK rat in the region corresponding to Niddm1b. See, Galli et al., 1996, supra.

TABLE 3

Diabetes-associated phenotypes in Niddml congenics and F344 at age 185 days

| Phenotype | F344 (n = 9) | Niddm1b/F344 (n = 11) | Niddm1b (n = 10) | Niddm1i/F344 (n = 8) | Niddm1i (n = 10) |
| --- | --- | --- | --- | --- | --- |
| Weight (g) | 365 ± 9 | 354 ± 4 | 389 ± 4* | 356 ± 4 | 350 ± 6 |
| Basal glucose (mmol/l) | 5.7 ± 0.1 | 5.6 ± 0.2 | 6.2 ± 0.1** | 5.9 ± 0.1 | 5.7 ± 0.1 |
| Basal insulin (pmol/l) | 378 ± 71 | 423 ± 48 | 631 ± 38** | 408 ± 47 | 472 ± 50 |
| Fat weight (g) | 10.5 ± 0.7 | 9.4 ± 0.2 | 12.4 ± 0.3* | 9.8 ± 0.4 | 10.2 ± 0.4 |
| Triglyceride (mmol/l) | 2.30 ± 0.09 | 2.07 ± 0.13 | 3.03 ± 0.16** | 2.25 ± 0.09 | 2.16 ± 0.14 |

TABLE 3-continued

Diabetes-associated phenotypes in Niddm1 congenics and F344 at age 185 days

| Phenotype | F344 (n = 9) | Niddm1b/F344 (n = 11) | Niddm1b (n = 10) | Niddm1i/F344 (n = 8) | Niddm1i (n = 10) |
| --- | --- | --- | --- | --- | --- |
| Total cholesterol (mmol/l) | 2.12 ± 0.05 | 1.87 ± 0.03*** | 2.22 ± 0.05 | 2.18 ± 0.02 | 2.31 ± 0.08 |
| HDL cholesterol (mmol/l) | 0.96 ± 0.02 | 0.87 ± 0.02** | 1.05 ± 0.03* | 1.05 ± 0.02** | 1.08 ± 0.04** |

All values are given as mean ± standard error of the mean (sem).
Each congenic strain was compared with F344 (Student's T-test) and significant differences are indicated: *P < 0.05, P < 0.01 *P < 0.001.

In Niddm1i rats, the postprandial glucose levels at 95 days were significantly higher when compared with F344 rats (Table 2). Furthermore, similar to the first experimental series (FIG. 2), serum insulin levels during IPGTT were lower in Niddm1i rats (Table 2). Also, in 65 day old Niddm1i rats, the insulin levels were lower compared with F344 rats, indicating a pronounced and early B-cell defect in Niddm1i. At 15 min post glucose-injection, insulin levels in Niddm1i rats were 56% of that in F344 rats, despite slightly elevated blood glucose levels (Table 1). No major differences in glucose or insulin levels were found between Niddm1i/F344 and F344 rats at 65 or 95 days. At the age of 185 days, neither Niddm1i nor Niddm1i/F344 differed from F344 for any of the analyzed phenotypes, except for higher HDL cholesterol in both Niddm1i and Niddm1i/F344 (Table 3).

Example 4

Insulin action in adipocytes: To characterize further the Niddm1 phenotype, adipocytes were isolated from the epididymal fat depot of rats at age 75 days (Niddm1i, Niddm1b, F344, and GK). Lipogenesis was determined as incorporation of radioactive glucose into lipids in response to increasing concentrations of insulin. Compared with F344 rats, adipocytes from both Niddm1b and Niddm1i rats had significantly lower basal and insulin induced lipogenesis, but were significantly higher than adipocytes from GK rats, which demonstrated severely reduced insulin action (FIG. 3). There was no significant difference between the congenic strains Niddm1b and Niddm1i. The $EC_{50}$ of insulin induced lipogenesis revealed no inter-strain difference in insulin sensitivity. In addition, lipolysis was studied by measuring glycerol release from isolated adipocytes. No significant differences were observed in either basal lipolysis or noradrenaline induced lipolysis. This demonstrates that the observed differences in insulin action reflect a pathway-specific defect and not a general adipocyte dysfunction.

Example 5

Figure 4:
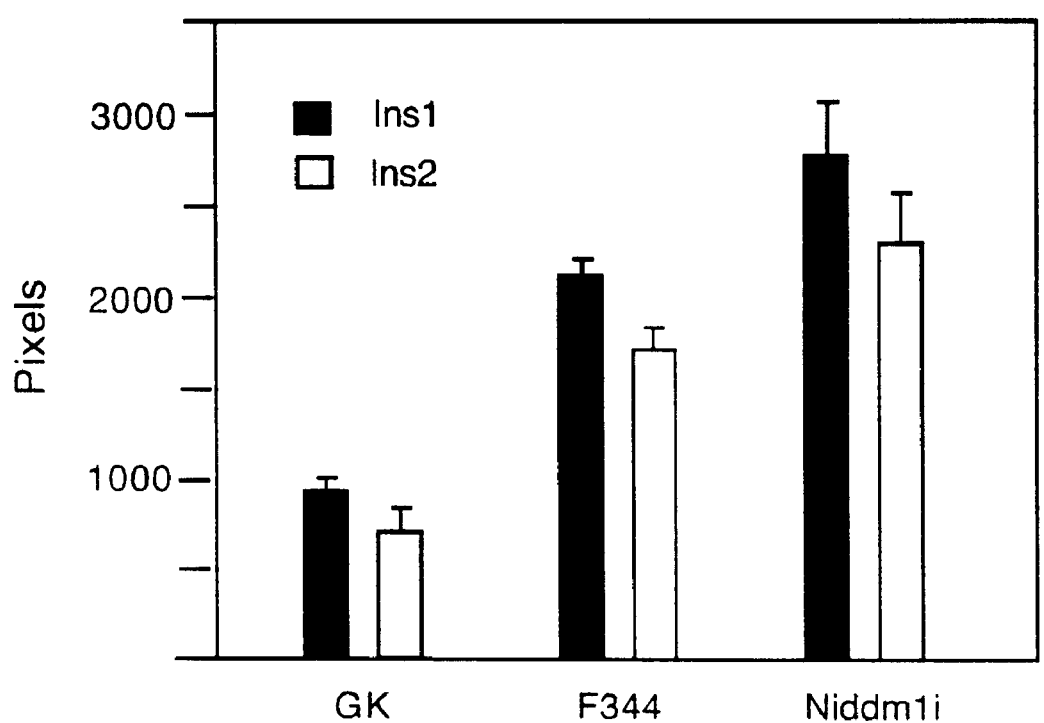
FIG. 4 is a graph that depicts quantitative analysis of insulin RNA in GK, F344, and Niddm1 rats. Results are shown as mean±sem. The amounts of RNA are expressed as pixels, and were calculated from band intensities using phosphorimaging techniques.

Candidate gene function and syntenic conservation: The insulin 1 gene (Ins1) is located in the GK interval contained in Niddm1i and was a candidate for mutations causing the impaired glucose homeostasis. A difference in the Ins1 promoter sequence between GK and F344 rats has been reported at nucleotide position −258 bp relative to the transcription start site, although both strains contain a similar relative abundance of Ins1 and Ins2 mRNA in pancreas. Galli et al., 1996, supra. To investigate a potential role of this genetic variation in more detail, the pancreatic levels of steady state mRNA for Ins1 and Ins2 were estimated by semiquantitative RT-PCR in GK, F344, and Niddm1i rats (n=4) after a fasting period of 7 h and after 2 h of repeated glucose injections (FIG. 4). Compared with F344, the total insulin mRNA level was 30% higher in Niddm1i rats, in spite of the impaired insulin response demonstrated during IPGTT. The relative expression of Ins1 and Ins2, however, did not differ among the strains in either the basal or the glucose stimulated state. Thus, Ins1 is excluded as a candidate for the Niddm1i phenotype. The insulin RNA data show that the defect in insulin secretion observed in Niddm1i is located downstream of the regulation of insulin transcription.

Information of the corresponding homologous regions to Niddm1 in human and mouse is important for locating candidate genes, and for comparisons of the Niddm1 rat locus with other susceptibility loci linked to type II diabetes or its associated phenotypes in the human or the mouse. Roughly guided by previously mapped genes on rat chromosome 1 and conserved synteni between rat, human, and mouse, three new genes were mapped to the Niddm1 locus on rat chromosome 1. These were the genes encoding Janus kinase 2 (JAK2), 5-hydroxytryptamine receptor 7 (HTR7), and pancreatic lipase (PNLIP) (indicated in bold in FIG. 1). This demonstrates homology between the Niddm1 locus and human chromosome region 9p24 and, furthermore, confirms the syntenic conservation between rat chromosome 1, human chromosome region 10q24–26, and mouse chromosome 19 (Table 4).

TABLE 4

Genes in the Niddm1 region on rat chromosome 1 and localization of the human and mouse homologues*

| | | Chromosomal Localization | | |
| --- | --- | --- | --- | --- |
| Gene Name | Gene Symbol | Rat† | Human | Mouse‡ |
| Glutathione-S-transferase, pi | Gstp | 118 | 11q13 | 19 (0) |
| Phosphorylase, glycogen; muscle | Pygm | 118 | 11q13.1 | 19 (2) |
| Janus kinase 2 | Jak2 | 133 | 9p24 | 19 (24) |
| 5-hydroxytryptamine receptor 7 | Htr7 | 140 | 10q24 | 19 (33) |
| Cytochrome P450, subfamily IIc | Cyp2c | 142 | 10q24.1 | 19 (27) |
| Glutamic-oxaloacetic transaminase 1 | Got1 | 144 | 10q24.1–25.1 | 19 (37) |
| Insulin 1 | Ins1 | 154 | NA | 19 (49) |
| Pancreatic lipase | Pnlip | 159 | 10q26.1 | 19 (29) |

Background information was obtained from Rat Genome Database (http://ratmap.gen.gu.se/), Mouse Genome Informatics (http://www.informatics.jax.org/), and Genome Database (http://www.gdb.org/).
†Distance in cM from marker D1Mgh2, located in the centromeric end of rat chromosome 1.
‡Distance in cM from the centromere is shown in parentheses preceded by the chromosome number

Example 6

Figure 5:
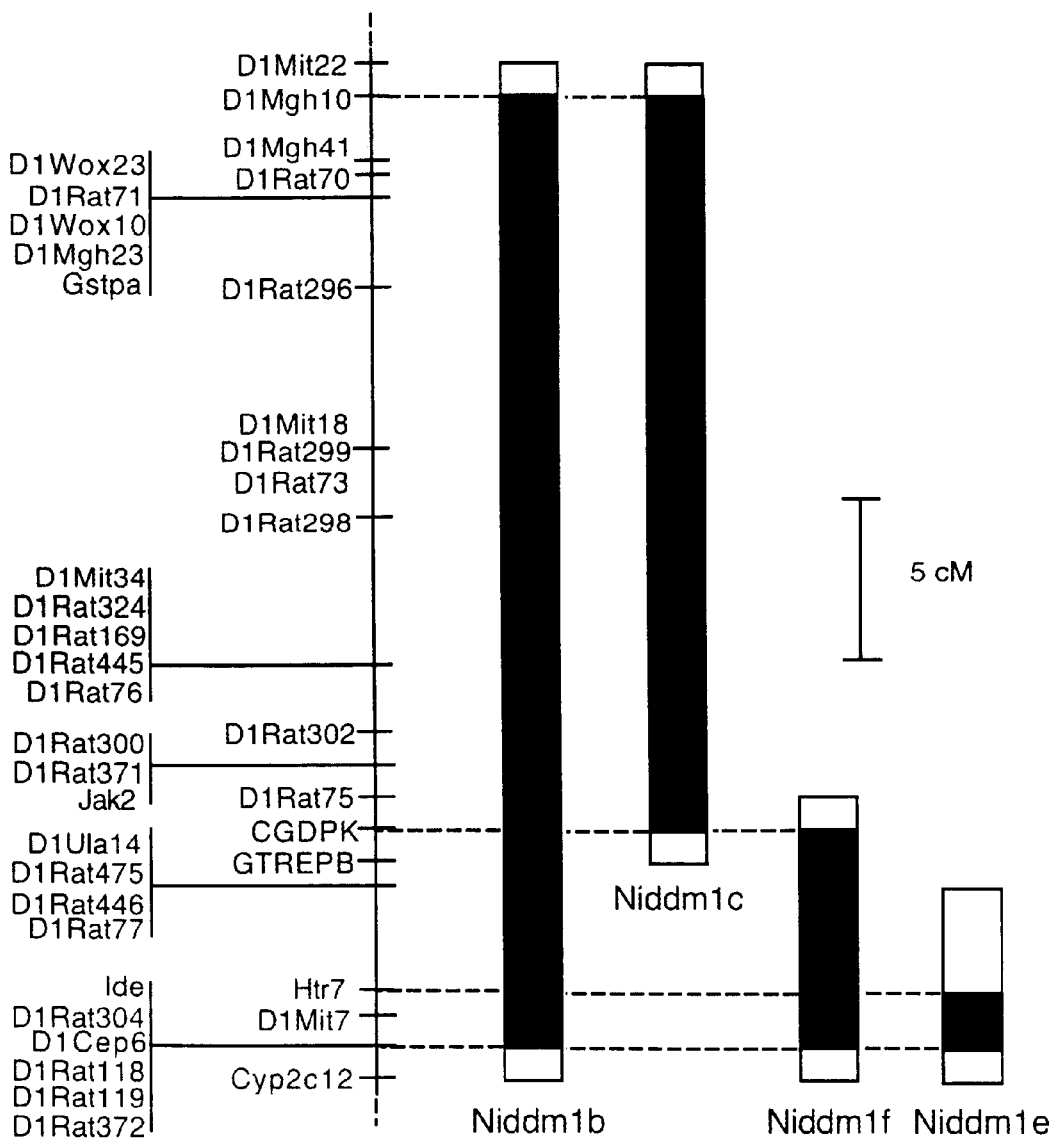
FIG. 5 is a genetic map of part of rat chromosome 1 in congenic rat strains Niddm1b, Niddm1c, Niddmf, and Niddm1e. The extents of GK derived genomic intervals are displayed as black bars for the four congenic strains. White bars indicate genomic intervals spanning the crossover points between GK and F344 derived alleles, as defined by the closest flanking markers.

Congenic substrains and associated phenotypes: For further characterization of Niddm1b, congenic sub-lines were established. Niddm1b rats were backcrossed to F344 and recombinants were identified within the GK interval. Three recombinants, covering distinct parts of the GK interval were selected, and homozygous lines were established for the GK-allele. The resulting congenic strains, F344.GK-Niddm1c (Niddm1c), F344.GK-Niddm1f (Niddm1f), and F344.GK-Niddm1e (Niddm1e) maintained 23±1 cM, 7.6±1 cM, and 3.7±2 cM, respectively, of GK alleles (FIG. 5).

Since an intraperitoneal glucose tolerance test was used to identify Niddm1 as well as to define the Niddm1b and Niddm1i sub-loci, the same test was applied to characterize the 1c, 1e, and 1f strains. To map the susceptibility gene within Niddm1b, rats from the new congenic sub-strains (Niddm1e, Niddm1f, and Niddm1c) and F344 were subjected to IPGTT at 95 days of age. Similarly to Niddm1b, postprandial glucose levels in both Niddm1e and Niddm1f were significantly higher than in F344 (Table 5). The most pronounced difference was observed at 30 min after glucose injection, when the glucose levels were 21% higher in both Niddm1e and Niddm1f. The basal and 30 min insulin levels also were significantly higher than in F344. No significant differences in glucose or insulin levels were observed between Niddm1c and F344.

TABLE 5

Niddm1e, Niddm1f, Niddm1c and F344

| Phenotype | F344 (n = 12) Mean ± sem | Niddm1e (n = 10) Mean ± sem | P value | Niddm1f (n = 11) Mean ± sem | P value | Niddm1c (n = 11) Mean ± sem | P value |
|---|---|---|---|---|---|---|---|
| 65 days rats | | | | | | | |
| Weight (g) | 223 ± 4 | 195 ± 2 | 0.00001 | 211 ± 4 | NS | 201 ± 7 | 0.009 |
| Glucose 0 min | 5.6 ± 0.2 | 5.6 ± 0.2 | NS | 5.9 ± 0.2 | NS | 5.5 ± 0.1 | NS |
| Glucose 15 min | 16.6 ± 0.7 | 15.7 ± 0.9 | NS | 17.5 ± 0.7 | NS | 17.3 ± 0.3 | NS |
| Glucose 30 min | 10.1 ± 0.5 | 10.2 ± 0.7 | NS | 10.6 ± 0.4 | NS | 9.0 ± 0.4 | NS |
| Glucose 60 min | 5.4 ± 0.1 | 5.2 ± 0.2 | NS | 5.7 ± 0.2 | NS | 5.3 ± 0.1 | NS |
| Glucose 90 min | 5.4 ± 0.1 | 5.4 ± 0.5 | NS | 6.1 ± 0.2 | 0.008 | 5.7 ± 0.2 | NS |
| Insulin 0 min | 114 ± 13 | 102 ± 16 | NS | 145 ± 10 | NS | 75 ± 12 | 0.04 |
| Insulin 15 min | 2039 ± 194 | 1335 ± 195 | 0.02 | 2039 ± 146 | NS | 1436 ± 289 | NS |
| Insulin 30 min | 1112 ± 321 | 725 ± 137 | NS | 1159 ± 166 | NS | 749 ± 163 | NS |
| 95 days rats | | | | | | | |
| Weight (g) | 268 ± 4 | 276 ± 3 | NS | 277 ± 5 | NS | 258 ± 5 | NS |
| Glucose 0 min | 5.3 ± 0.1 | 5.4 ± 0.1 | NS | 5.7 ± 0.1 | 0.01 | 5.6 ± 0.2 | NS |
| Glucose 15 min | 15.4 ± 0.4 | 17.2 ± 0.7 | 0.03 | 17.3 ± 0.7 | 0.03 | 15.6 ± 0.6 | NS |
| Glucose 30 min | 12.0 ± 0.3 | 14.5 ± 0.3 | 0.00005 | 14.5 ± 0.5 | 0.0002 | 11.8 ± 0.5 | NS |
| Glucose 60 min | 6.8 ± 0.1 | 8.4 ± 0.3 | 0.0001 | 7.7 ± 0.2 | 0.0008 | 6.1 ± 0.2 | 0.01 |
| Glucose 90 min | 6.3 ± 0.1 | 6.7 ± 0.1 | NS | 6.8 ± 0.3 | NS | 6.6 ± 0.2 | NS |
| Insulin 0 min | 201 ± 25 | 331 ± 24 | 0.001 | 441 ± 37 | 0.0003 | 246 ± 57 | NS |
| Insulin 15 min | 2162 ± 167 | 2425 ± 102 | NS | 2431 ± 215 | NS | 2265 ± 373 | NS |
| Insulin 30 min | 1626 ± 164 | 2497 ± 93 | 0.0003 | 2405 ± 162 | 0.004 | 1554 ± 320 | NS |
| 120 days rats | | | | | | | |
| Weight (g) | 303 ± 4 | 314 ± 4 | NS | 309 ± 5 | NS | NA | |
| Basal glucose | 5.8 ± 0.1 | 5.0 ± 0.1 | 0.0001 | 5.3 ± 0.2 | 0.02 | NA | |
| Basal insulin | 276 ± 23 | 386 ± 55 | NS | 390 ± 36 | 0.01 | NA | |

For further characterization, the congenic strains were studied after treatment with a diet containing a high amount of fat. Niddm1e, Niddm1f and F344 rats were treated with the high fat diet described in Example 1, starting at the age of 120 days. Rats were subjected to IPGTT and the basal levels of triglyceride, total cholesterol, and HDL cholesterol were determined at 225 days of age; subsequently the animals were sacrificed, and the epididymal fat depots were weighed. At this age, postprandial glucose levels were still significantly higher in Niddm1e and Niddm1f as compared with F344 (Table 6). In contrast to the IPGTT at 95 days, the differences were more pronounced at the later time points after glucose injection (Table 5). At 90 min after injection, the glucose levels in both congenics were approximately 30% higher than in F344. The basal insulin levels were significantly higher in the congenics than in F344, but the insulin levels after glucose injection were not. At this age, increases in both body weight and epididymal fat weight were observed, however, were only significantly increased in Niddm1e.

TABLE 6

| Phenotype | F344 (n = 12) Mean ± sem | Niddmle(n = 10) Mean ± sem | P value | Niddmlf(n = 11) Mean ± sem | P value |
|---|---|---|---|---|---|
| Rats 185 days | | | | | |
| weight | 373 ± 5 | 386 ± 4 | NS | 379 ± 7 | NS |
| Basal glucose | 4.5 ± 0.2 | 5.3 ± 0.1 | 0.001 | 5.2 ± 0.8 | 0.02 |
| Basal insulin | 459 ± 42 | 553 ± 71 | NS | 578 ± 24 | 0.03 |
| Rats 220 days | | | | | |
| Weight (g) | 377 ± 6 | 400 ± 5 | 0.01 | 384 ± 8 | NS |
| Glucose 0 min | 4.8 ± 0.1 | 4.9 ± 0.1 | NS | 4.9 ± 0.1 | NS |
| Glucose 15 min | 17.1 ± 0.3 | 20.3 ± 1.3 | 0.04 | 17.1 ± 1.4 | NS |
| Glucose 30 min | 17.7 ± 0.8 | 19.4 ± 0.6 | NS | 18.5 ± 0.7 | NS |
| Glucose 60 min | 14.6 ± 0.7 | 17.6 ± 1.0 | 0.02 | 17.8 ± 0.6 | 0.005 |
| Glucose 90 min | 10.4 ± 0.4 | 13.9 ± 0.9 | 0.0009 | 13.4 ± 0.8 | 0.001 |
| Insulin 0 min | 337 ± 16 | 480 ± 46 | 0.003 | 410 ± 24 | 0.02 |
| Insulin 15 min | 1069 ± 109 | 1166 ± 143 | NS | 985 ± 111 | NS |
| Insulin 30 min | 1217 ± 77 | 2533 ± 144 | NS | 1049 ± 71 | NS |
| 230 days rats | | | | | |
| Weight (g) | 368 ± 4 | 391 ± 6 | 0.004 | 375 ± 8 | NS |
| Fat weight | 8.5 ± 0.3 | 10.6 ± 0.5 | 0.0009 | 9.3 ± 0.4 | NS |
| Basal insulin | 314 ± 31 | 413 ± 24 | 0.02 | 454 ± 47 | 0.02 |
| Cholest | 4.35 ± 0.13 | 4.33 ± 0.20 | NS | 4.13 ± 0.15 | NS |
| Trig | 0.66 ± 0.03 | 0.76 ± 0.06 | NS | 0.61 ± 0.02 | NS |
| HDL | 1.23 ± 0.07 | 0.97 ± 0.02 | 0.003 | 1.12 ± 0.03 | NS |
| LDL | 2.80 ± 0.08 | 3.00 ± 0.17 | NS | 2.77 ± 0.16 | NS |

Figure 6A:
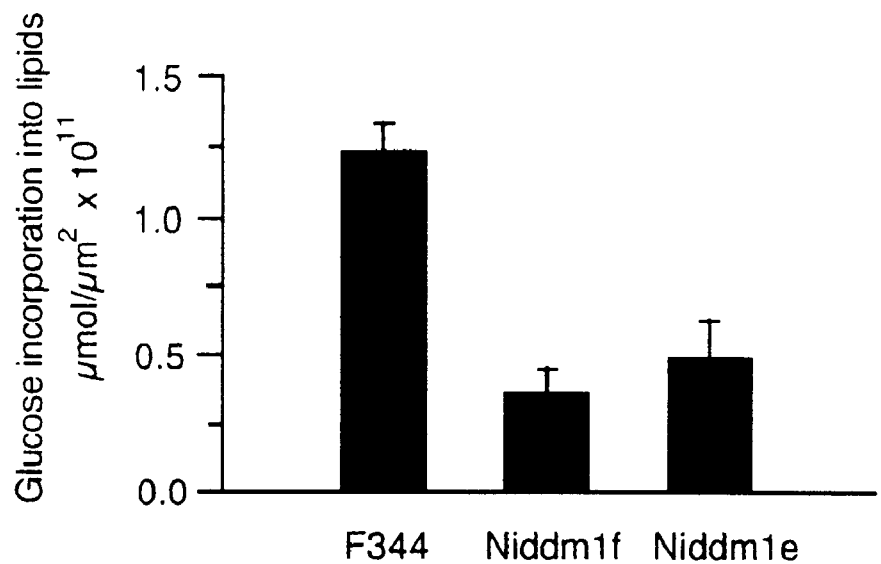
FIGS. 6A–6B are graphs that depict lipogenesis in adipocytes isolated from epididymal fat. Adipocytes were isolated from two-month old male F344 (n=6), Niddm1f (n=5), and Niddm1e (n=4) rats, and incubated for 2 h with insulin (0–20,000 $\mu$U/ml).
Figure 6B:
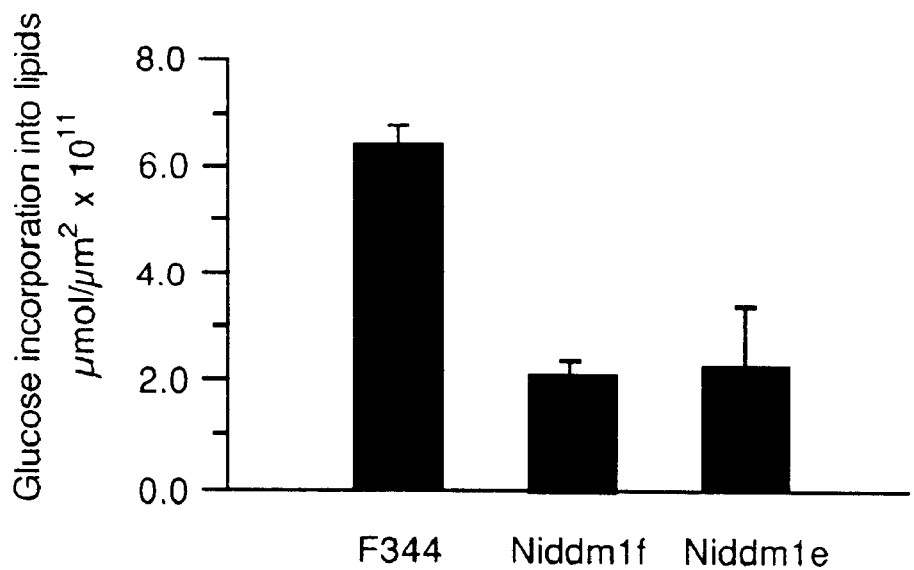

As described in Example 2, basal and insulin-induced lipogenesis in Niddm1b was significantly reduced as compared with F344. A similar test was performed with the Niddm1b sub-strains, Niddm1e and Niddm1f, and control F344. Lipogenesis also was reduced in both Niddm1e and Niddm1f compared with F344 (FIG. 6). Based on these data, the Niddm1b diabetes susceptibility gene/genes is located in the 3.7 cM GK interval of Niddm1e.

Example 7

DNA sequence analysis and expression of Ide: Candidate genes were identified using genetic mapping data from humans and mice. Synteny is conserved between the Niddm1 region on rat chromosome 1 and human chromosomes 9 and 10 and mouse chromosome 19. One gene that has not previously been considered a candidate for diabetes is the gene encoding insulin degrading enzyme (IDE), which mapped to human chromosome 10q24 and mouse 19. The Ide gene was genetically mapped on rat chromosome 1 within the GK interval of Niddm1e, by restriction fragment length polymorphism (RFLP) analysis (FIG. 5).

Figure 7:
FIG. 7 is a schematic of the translated part of the gene encoding a rat insulin degradation enzyme (IDE).

To investigate the possibility that changes in the IDE protein structure could explain the phenotype of Niddm1e, the cDNA sequence of IDE was determined in both GK and F344 rats. Sequencing the complete translated part of the gene revealed three nucleotide differences between GK and F344 rats, one in the 5'-end (codon 18) and two in the 3' end (codons 890 and 934) of the coding region (FIG. 7). Two of these resulted in amino-acid changes, a CAC to CGC change at codon 18 resulted in the substitution of Arginine for histidine and a GCG to GTG transition at codon 890 resulted in the substitution of valine for alanine. The third variant was silent, changing the last base of codon 934 (GAT to GAC). Additionally, the IDE cDNA sequences were determined in 12 other rat strains (DA, PVG/RT1, PVG/Bk, Lew, ACI, BN, Cop, BB, W, SD, FRL, and FSL). The A890V variation was unique for GK, while H18R was also found in the strains, DA, ACI, SD, FRL, and FSL (Table 7).

TABLE 7

Sequence variants in the Ide gene of various rat strains

| Strain | Codon 18 | Codon 890 | Codon 934 |
|---|---|---|---|
| GK | CGC (Arg) | GTG (Val) | GAC |
| F344 | CAC (His) | GCG (Ala) | GAT |
| PVG | CAC (His) | GCG (Ala) | GAT |
| LEW | CAC (His) | GCG (Ala) | GAT |
| BN | CAC (His) | GCG (Ala) | GAT |
| COP | CAC (His) | GCG (Ala) | GAT |
| BB | CAC (His) | GCG (Ala) | GAT |
| Wistar | CAC (His) | GCG (Ala) | GAT |
| DA | CGC (Arg) | GCG (Ala) | GAT |
| ACI | CGC (Arg) | GCG (Ala) | GAT |
| SD | CGC (Arg) | GCG (Ala) | GAC |
| FRL | CGC (Arg) | GCG (Ala) | GAC |
| FSL | CGC (Arg) | GCG (Ala) | GAC |

Figure 8:
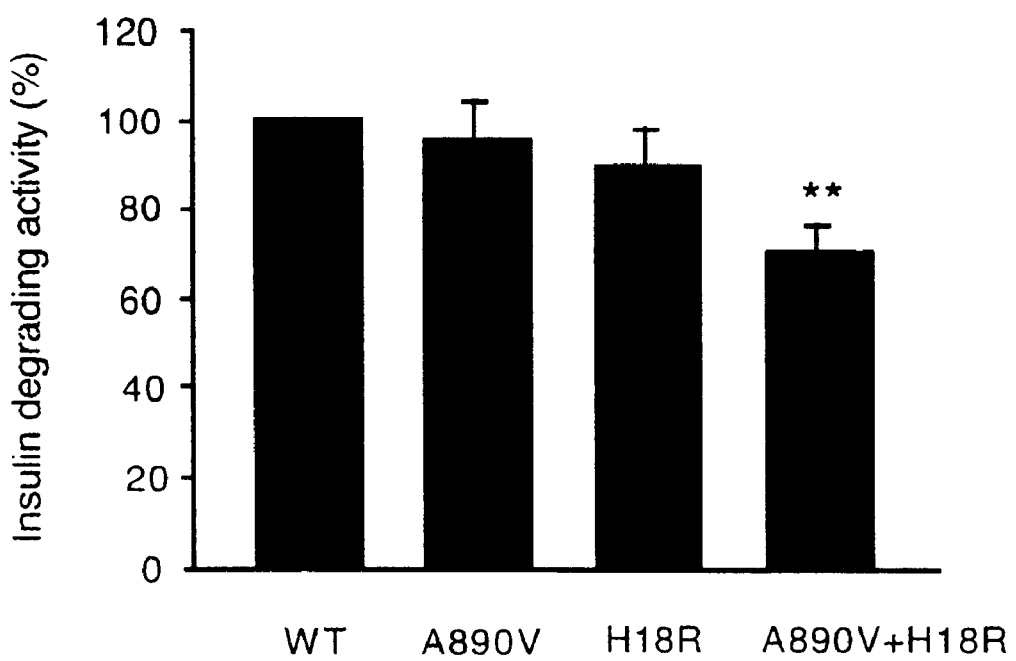
FIG. 8 is a graph that depicts insulin degrading activities of wild-type IDE and IDE variants A890V (i.e, valine for alanine at amino acid 890), H18R (i.e, arginine for histidine at amino acid 18), and A890V+H18R in intact COS-1 cells. All values are from four separate transfections and are expressed as the percentage of wild type activity (cells transfected by pCMV4-Ide from F344 rat), which is arbitrarily defined as 100%. Within each experiment, the background COS-1 insulin degrading activity was subtracted from each individual value and activities were corrected for both the total protein content and βgalactosidase activity. Actual values (mean±sem) for A890V, H18R, and A890R+H18R are 95±9, 89±8, and 69±6%, respectively.

To study the effect of the GK variant of IDE, insulin degrading activity was determined in an in vitro expression system. IDE was over-expressed in transfected COS1 cells and the ability of cell lysates to hydrolyze insulin were studied. Western blot analysis with anti-IDE antibodies confirmed expression of transfected IDE cDNAs. The two amino-acid variations in the GK allele, H18R and A890V, were studied separately or in combination. Insulin degrading activity in intact cells transfected with the GK allele containing both H18R and A890V, was decreased by 34% (p<0.001) compared with control (FIG. 8). When the two variants were analyzed separately, only H18R showed slightly reduced activity (89%) of wild-type, p<0.001 as compared with control, while A890V was normal, indicating a synergistic effect of the two variants. In cell lysates, no differences were observed for the GK allele on insulin degradation compared to the normal variant.

Niddm1e displayed elevated postprandial glucose levels, impaired basal and insulin induced lipogenesis in isolated adipocytes, increased body weight and epididymal fat mass, and hyperinsulinemia. Furthermore, Niddm1e were treated with high fat diet under a period of 3.5 months and subsequently the rats were subjected to IPGTT at the age of 7.5 months. At this age, the most pronounced difference in glucose levels as compared with F344 were observed at the later time points after glucose injection and not as in younger animals at the earlier time points. Thus, the diabetes locus Niddm1b is redefined to a 3 cM region in the congenic strain Niddm1e.

These data indicate that a gene encoding IDE partly explains the diabetic phenotype in the GK rat and through some of its multiple actions in the cell, causes hyperglycemia and insulin resistance in Niddm1e. Several other studies have shown decreased insulin clearance associated with insulin resistance and diabetes, suggesting that a reduction in insulin degradation could mediate a diabetic phenotype. A possible molecular explanation is that in peripheral tissues, a decreased intra-cellular degradation of insulin bound to its receptor could inhibit the re-circulation of the insulin receptor back to the cell membrane and thus lowering the number of available receptors on the cell membrane.

Example 8

NiddmC congenic animals: Genome-wide linkage analysis, as described in Galli et al. 1996, supra, was used to localize chromosome regions demonstrating genetic linkage to diabetes-associated phenotypes. The F2-population of intercross progeny generated between GK and F344 rats was analyzed with all F2 animals together, and separately for sex and reciprocal cross, in favor of linkage in a dense, genome-wide search for linkage to diabetes-associated phenotypes. Table 8 describes loci with a LOD (logarithm of odds ratio) greater than 3 for at least one diabetes-associated phenotype. The marker located in the middle of each chromosome region is shown in Table 8, and is located in the center of approximately 25 cM, which encompass each of these QTLs for diabetes-associated phenotypes.

Congenic animals of the NiddmC series (NiddmC2, NiddmC3, NiddmC5, NiddmC7, NiddmC9A, NiddmC9B, NiddmC10, NiddmC11, NiddmC13, NiddmC18, NiddmC (13+15), and NiddmC(9+13+15)) were generated by backcrossing GK onto F344 and choosing progeny which had lost maximum GK derived (donor) alleles in each generation (marker assisted selection, see, Whittaker et al., *Genet Res.*, 66(3):255–65, 1995;and Darvasi, *Nat Genet.*, 18(1):19–24, 1998.

The microsatellite markers listed in Table 9 cover QTLs identified in F2 progeny from intercrossing GK and F344. Theses markers distinguish between GK and F344 alleles and display the GK-allele after backcrossing to generate congenic animals. The diabetes-associated QTLs, which were selected for during generation of the respective congenic strain, are listed in Table 9, followed by the microsatellite markers that define GK-derived alleles within each QTL. All other tested markers outside this selected chromosome region exhibited an F344-specific genotype. These background markers were located approximately every 50 cM along the rat genome and were specifically selected against by choosing the progeny in each backcross generation that had lost the maximum amount of GK-derived (donor) background.

TABLE 8

List of Markers with a LOD score >3

| Chromosome | Marker at LOD max | Highest LOD-score for diabetes-associated phenotype |
|---|---|---|
| C1 | D1Mit9 | 4.0 |
| c1 | D1Mgh40 | 3.2 |
| c1 | D1Mit18 | 3.6 |
| c1 | D1Mit34 | 7.3 |
| c1 | D1Mgh25 | 8.7 |
| c1 | GTREPB | 3.2 |
| c1 | D1Mit7 | 8.0 |
| c1 | D1Mgh24 | 8.5 |
| c1 | D1Mgh13 | 3.6 |
| c1 | D1Mit8 | 5.7 |
| c1 | D1Mit14 | 3.0 |
| c2 | D2Mit11 | 4.6 |
| c2 | D2Mit14 | 3.2 |
| c2 | D2N91 | 3.4 |
| c3 | D3Mit8 | 3.2 |
| c3 | D3Rat27 | 3.1 |
| c4 | D4Mit28 | 3.9 |
| c7 | D7Mit28 | 4.4 |
| c7 | D7Rat27 | 8.6 |
| c7 | D7Rat106 | 3.8 |
| c7 | D7Mit6 | 7.4 |
| c7 | D7Mgh23 | 3.1 |
| c7 | D7Mit11 | 3.5 |
| c7 | D7Mit9 | 3.1 |
| c9 | D9Mgh3 | 4.6 |
| c9 | D9Rat104 | 6.9 |
| c10 | D10Rat64 | 3.3 |
| c10 | D10Mit8 | 4.1 |
| c10 | D10Mgh23 | 5.2 |
| c10 | D10Mgh5 | 5.4 |
| c10 | D13Mit11? | 3.8 |
| c12 | D12Rat22 | 3.6 |
| c13 | D13Mgh16 | 4.6 |
| c15 | D15Rat25 | 3.1 |
| c17 | D17Mgh6 | 3.7 |
| c18 | D18Mit11 | 4.2 |
| c19 | D19Mgh10 | 3.5 |
| c20 | D20Mit5 | 3.2 |
| c20 | D20Rat29 | 4.7 |
| x | DXMgh8 | 4.9 |
| x | DXRat16 | 5.5 |
| x | DXRat20 | 7.0 |
| x | DXRat103 | 4.2 |

TABLE 9

NiddmC Congenic Animals

| | |
|---|---|
| NiddmC2: | D2Mgh5, D2Mgh15, D2Mit10, D2Mit11, D2Mgh30, D2Mit22, D2Mgh11, and D2Arb24. |
| NiddmC3: | D3Mgh19, D3Mit10, and D3Mgh8,and D3Mgh6.. |
| NiddmC5: | D5Mgh5, D5Mit10, D5Mit2, D5Mit11, D5Mit4, D5Mit5, and D5Mgh23. |
| NiddmC7: | D7Mgh11, D7Mit23, D7Mit7, D7Mit22, D7Mit6, D7Mgh10, and D7Mit5. |
| NiddmC9A: | D9Mgh3, D9Mit4, D9Mit2, IGFBP5X, and GDNPN1. |
| NiddmC9B: | D9Mgh3, and D9Mit4. |
| NiddmC10: | D10Mit15, D10Mit16, D10Mit18, D10Mit9, D2Mit11, D10Mgh6, D10Mit13, D10Mgh5, D10Mit12, D10Mgh4, and D10Mit11. |
| NiddmC11: | D11Mgh5, D11Mgh4, D11Mgh3, and D11Mgh2. |
| NiddmC13: | D13Mgh16, D13Mgh2, D13Mit2, and D13Mit5. |
| NiddmC18: | D18Mit4, D18Mgh5, D18Mgh11, D18Mgh6, and D18Mit11. |
| NiddmC(13 + 15) | D13Mgh16, D13Mgh2, D13Mit2, D13Mit5, BMYO, D15Mgh15, D15Mgh8, and D15Mco2 |
| NiddmC(9 + 13 + 15): | D9Mit4, D9Mit2, D13Mit2, D13Mit5, D15Mgh8, and D15Mgh9. |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. A congenic rat comprising genetic material of a donor Goto-Kakizaki (GK) rat and a recipient rat, said congenic animal exhibiting a type II diabetes phenotype, wherein less than one chromosome of said congenic rat's genome is derived from said donor rat, wherein said genetic material from said donor is necessary for exhibition of said type II diabetes phenotype in said congenic rat, and wherein said genetic material derived from said donor is selected from a genomic interval selected from the group consisting of NiddmC, Niddm1a, Niddm1b, Niddm1c, Niddm1d, Niddm1e, Niddm1f, Niddm1g, Niddm1h, and Niddm1i.

2. The rat of claim 1, wherein said congenic rat is marker-defined.

3. The rat of claim 1, wherein less than 50 cM of said congenic animal's genome is derived from said donor.

4. The rat of claim 1, wherein less than about 20 cM of said congenic rat's genome is derived from said donor.

5. The rat of claim 1, wherein less than about 10 cM of said congenic rat's genome is derived from said donor.

6. The rat of claim 1, wherein less than about 5 cM of said congenic rat's genome is derived from said donor.

7. The rat of claim 1, wherein said type II diabetes phenotype is selected from the group consisting of elevated postprandial glycemia, hypertension, glucose intolerance, insulin resistance, abnormal insulin secretion, reduced insulin action, increased body weight, dyslipidemia, hyperinsulinemia, impaired lipogenesis, altered glycogen metabolism, altered coagulation atherosclerosis, altered kidney function, altered nerve function, altered eye function, obesity, and inflammation.

8. The rat of claim 1, wherein said genetic interval is a Niddm1a genomic interval.

9. The rat of claim 1, wherein said genomic interval is a Niddm1e genomic interval.

10. The rat of claim 1, wherein said NiddmC genomic interval is selected from the group consisting of NiddmC2, NiddmC3, NiddmC5, NiddmC7, NiddmC9A, NiddmC9B, NiddmC10, NiddmC11, NiddmC13, NiddmC18, NiddmC(13+15), and NiddmC(9+13+15).

11. The rat of claim 1, wherein mitochondria of said congenic rat are derived from either said recipient rat or said donor.

12. The rat of claim 1, wherein mitochondria of said congenic rat are derived from said recipient.

13. An isolated cell of the congenic rat of claim 1.

14. The cell of claim 14, wherein said cell is selected from the group consisting of adipocytes, mesangial cells, hepatic cells, pancreatic cells, muscle cells, endothelial cells, and neural cells.

15. A tissue culture derived from the congenic rat of claim 1.

16. The tissue expant of claim 15, wherein said expant is selected from the group consisting of adipose tissue, mesangial tissue, hepatic tissue, pancreatic tissue, muscle tissue, blood-vessel tissue, and neural tissue.

17. A congenic rat population comprising a plurality of congenic rats, said congenic rats exhibiting a plurality of type II diabetes phenotypes, wherein each congenic rat within said plurality of congenic rats comprises genetic material from a donor GK rat and a recipient rat, wherein said population comprises a congenic rat having about 0.1% of said congenic rat's genome derived from said donor rat and a congenic rat having about 50% of said congenic rat's genome derived from said donor rat, and wherein said genetic material from said donor rat is necessary for exhibition of said type II diabetes phenotype in each said congenic rat, wherein said congenic rat has a genomic interval from said donor rat, said genomic interval selected from the group consisting of NiddmC, Niddm1a, Niddm1b, Niddm1c, Niddm1d, Niddm1e, Niddm1f, Niddm1g, Niddm1h, and Niddm1i.

18. A method for testing a pharmaceutically active compound comprising:
 a) administering a test compound to a congenic animal exhibiting a type II diabetes phenotype, wherein said congenic rat comprises genetic material of a donor GK rat and a recipient animal, wherein less than 50 cM of said congenic rat's genome is derived from said donor rat, and wherein said genetic material from said donor is necessary for expression of said type II diabetes phenotype in said congenic rat; and wherein said genetic material derived from said donor is selected from a genomic interval selected from the group consisting of NiddmC, Niddm1a, Niddm1b, Niddm1c, Niddm1d, Niddm1e, Niddm1f, Niddm1g, Niddm1h, and Niddm1i; and
 b) evaluating said test compound for an effect on at least one type II diabetes phenotype in said congenic rat.

19. The method of claim 18, wherein said genomic interval is a Niddm1a genetic interval.

20. The method of claim 18, wherein said genomic interval is a Niddm1e genetic interval.

21. The method of claim 18, wherein said animal comprises a cross between two congenic parent animals, said parent animals having distinct congenic intervals.

22. The method of claim 18, wherein said NiddmC genomic interval is selected from the group consisting of NiddmC2, NiddmC3, NiddmC5, NiddmC7, NiddmC9A, NiddmC9B, NiddmC10, NiddmC11, NiddmC13, NiddmC18, NiddmC(13+15), and NiddmC(9+13+15).

23. A method for testing a pharmaceutically active compound comprising:
 (a) administering a test compound to a plurality of congenic rats exhibiting a plurality of type II diabetes phenotypes; and
 (b) evaluating said test compound for an effect on at least one type II diabetes phenotype, wherein each congenic rat within said plurality of congenic rats comprises genetic material from a donor GK rat and a recipient rat, wherein about 0.1% to about 50% of each congenic rat's genome is derived from said donor rat, and wherein said genetic material from said donor rat is necessary for exhibition of said type II diabetes phenotype in each said congenic rat, and wherein said genetic material from said donor rat is necessary for exhibition of said type II diabetes phenotype in each said congenic rat, wherein said congenic rat has a genomic interval from said donor rat, said genomic interval selected from the group consisting of NiddmC, Niddm1a, Niddm1b, Niddm1c, Niddm1d, Niddm1e, Niddm1f, Niddm1g, Niddm1h, and Niddm1i.

24. The method of claim 23, wherein said plurality of congenic rats comprises at least two rats having congenic intervals on different chromosomes.

25. An article of manufacture comprising isolated cells of a congenic rat exhibiting a type II diabetes phenotype, said congenic rat comprising genetic material of a donor GK rat and a recipient rat, wherein less than one chromosome of said congenic rat's genome is derived from said donor rat, wherein said genetic material from said donor is necessary for exhibition of said type II diabetes phenotype in said congenic rat, and wherein said genetic material derived from said donor is selected from a genomic interval selected from the group consisting of NiddmC, Niddm1a, Niddm1b, Niddm1c, Niddm1d, Niddm1e, Niddm1f, Niddm1g, Niddm1h, and Niddm1i.

26. The article of manufacture of claim 25, said article further comprising a label or package insert indicating said cells are useful for evaluating compounds that may be effective for alleviating type II diabetes phenotypes.

27. The article of manufacture of claim 25, wherein said NiddmC genomic interval is selected from the group consisting of NiddmC2, NiddmC3, NiddmC5, NiddmC7, NiddmC9A, NiddmC9B, NiddmC10, NiddmC11, NiddmC13, NiddmC18, NiddmC(13+15), and NiddmC(9+13+15).

28. The article of manufacture of claim 25, wherein said genomic interval is a Niddm1a genomic interval.

29. The article of manufacture of claim 25, wherein said genomic interval is a Niddm1e genomic interval.

30. A method of making a congenic rat comprising:
 (a) mating a donor GK rat and a recipient rat to produce a progeny rat; and
 (b) successively backcrossing said progeny rat with said recipient rat for at least 10 generations to produce said congenic rat, said congenic rat exhibiting a type II diabetes phenotype, wherein less than 50 cM of said congenic rat's genome is derived from said donor rat, and wherein said genetic material of said donor is necessary for exhibition of said type II diabetes phenotype in said congenic rat, and wherein said genetic material derived from said donor is selected from a genomic interval selected from the group consisting of NiddmC, Niddm1a, Niddm1b, Niddm1c, Niddm1d, Niddm1e, Niddm1f, Niddm1g, Niddm1h, and Niddm1i.

* * * * *

UNITED STATES PATENT AND TRADEMARK OFFICE
CERTIFICATE OF CORRECTION

PATENT NO.     : 6,465,714 B2
DATED          : October 15, 2002
INVENTOR(S)    : L. Holger Luthman and L.G. Joakim Galli It is certified that error appears in the above-identified patent and that said Letters Patent is hereby corrected as shown below:

<u>Column 47,</u>
Line 57, please delete "animal" and insert -- rat -- therefor.

<u>Column 48,</u>
Line 55, please delete "animal's" and insert -- rat's -- therefor.
Lines 56, 58 and 60, please delete "about."

<u>Column 49,</u>
Line 18, please delete "claim 14" and insert -- claim 13 -- therefor.
Line 22, please delete "culture derived from" and insert -- explant of -- therefor.
Line 24, please delete "expant" and insert -- explant -- therefor.
Lines 46, 49 and 65, please delete "animal" and insert -- rat -- therefor.
Line 52, please delete "expression" and insert -- exhibition -- therefor.
Line 66, after "prises" please insert -- a progent rat of --.
Lines 66 and 67, please delete "animals" and insert -- rats -- therefor.

Signed and Sealed this

Twenty-second Day of April, 2003

JAMES E. ROGAN
*Director of the United States Patent and Trademark Office*